United States Patent
Mata et al.

(10) Patent No.: US 12,232,743 B2
(45) Date of Patent: Feb. 25, 2025

(54) EXCLUSION DEVICE COVERS AND RELATED METHODS

(71) Applicant: AtriCure, Inc., Mason, OH (US)

(72) Inventors: Carol Ann Mata, Cincinnati, OH (US); Nikhil Kabbur, Cincinnati, OH (US); Lynn Ann Recker, Cincinnati, OH (US); Justin David Volz, West Chester, OH (US)

(73) Assignee: AtriCure, Inc., Mason, OH (US)

( * ) Notice: Subject to any disclaimer, the term of this patent is extended or adjusted under 35 U.S.C. 154(b) by 323 days.

(21) Appl. No.: 17/931,305

(22) Filed: Sep. 12, 2022

(65) Prior Publication Data
US 2023/0082963 A1 Mar. 16, 2023

Related U.S. Application Data

(60) Provisional application No. 63/243,322, filed on Sep. 13, 2021, provisional application No. 63/243,335, (Continued)

(51) Int. Cl.
*A61B 17/122* (2006.01)
*A61B 17/12* (2006.01)
(Continued)

(52) U.S. Cl.
CPC .... *A61B 17/1285* (2013.01); *A61B 17/12036* (2013.01); *A61B 17/12122* (2013.01);
(Continued)

(58) Field of Classification Search
CPC ... A61B 17/1227; A61B 17/12; A61B 17/122; A61B 17/08; A61B 17/083;
(Continued)

(56) References Cited

U.S. PATENT DOCUMENTS

| 7,645,285 B2 | 1/2010 | Cosgrove et al. |
| 10,166,024 B2 | 1/2019 | Williamson, IV et al. |
| (Continued) | | |

FOREIGN PATENT DOCUMENTS

WO 2020224625 11/2020

OTHER PUBLICATIONS

Aran Biomedical, Implantable Grade Polyester Yarn (PET), retreived from https://www.aranbiomedical.com/implantable-grade-polyester-yarn/ on Sep. 5, 2021.
(Continued)

*Primary Examiner* — Katherine M Shi
(74) *Attorney, Agent, or Firm* — Dorton & Willis LLP; Ryan Willis

(57) ABSTRACT

Exclusion devices for anatomical structures, and related instruments and related methods, are disclosed. An exclusion device may include a first clamping portion, a second clamping portion opposing the first clamping portion, and/or a biocompatible fabric cover at least partially sheathing the first clamping portion and/or the second clamping portion. The cover may be generally tubular and/or may define a relaxed circumference when the first clamping portion and the second clamping portion are in a closed configuration. At least a portion of the cover may be configured to stretch to a stretched circumference of about 2× to about 3× the relaxed circumference when the first clamping portion and the second clamping portion are reconfigured from the closed configuration to an open configuration.

20 Claims, 17 Drawing Sheets

Related U.S. Application Data filed on Sep. 13, 2021, provisional application No. 63/243,329, filed on Sep. 13, 2021, provisional application No. 63/243,313, filed on Sep. 13, 2021.

(51) Int. Cl.
| | |
|---|---|
| *A61B 17/128* | (2006.01) |
| *A61B 17/30* | (2006.01) |
| *A61N 1/39* | (2006.01) |
| *B21F 45/00* | (2006.01) |
| *B29C 65/00* | (2006.01) |
| *B29C 65/08* | (2006.01) |
| *A61B 17/00* | (2006.01) |
| *A61B 17/29* | (2006.01) |
| *B29K 667/00* | (2006.01) |
| *B29L 31/00* | (2006.01) |

(52) U.S. Cl.
CPC ........ *A61B 17/122* (2013.01); *A61B 17/1227* (2013.01); *A61B 17/30* (2013.01); *A61N 1/395* (2013.01); *A61N 1/3968* (2013.01); *B21F 45/008* (2013.01); *B29C 65/08* (2013.01); *B29C 66/1122* (2013.01); *B29C 66/729* (2013.01); *B29C 66/87445* (2013.01); *A61B 2017/00243* (2013.01); *A61B 2017/00371* (2013.01); *A61B 2017/00526* (2013.01); *A61B 2017/00632* (2013.01); *A61B 2017/00831* (2013.01); *A61B 2017/00946* (2013.01); *A61B 2017/2926* (2013.01); *B29K 2667/003* (2013.01); *B29K 2995/0056* (2013.01); *B29L 2031/753* (2013.01)

(58) Field of Classification Search
CPC ...... A61B 17/1285; A61B 2017/00243; A61B 17/12122; A61B 2017/00884; A61B 17/12036; A61B 2017/00632; A61B 2017/00831; A61B 2017/00867
See application file for complete search history.

(56) References Cited

U.S. PATENT DOCUMENTS

| | | |
|---|---|---|
| 2011/0046437 A1 | 2/2011 | Kassab et al. |
| 2012/0059400 A1* | 3/2012 | Williamson, IV ............................ A61B 17/1227 606/158 |
| 2018/0036007 A1 | 2/2018 | Fago et al. |
| 2019/0142428 A1 | 5/2019 | Widenhouse et al. |
| 2019/0231356 A1* | 8/2019 | Deville ............. A61B 17/1285 |
| 2020/0197014 A1 | 6/2020 | Deville et al. |
| 2021/0169489 A1 | 6/2021 | Deville et al. |

OTHER PUBLICATIONS

International Searching Authority/US, International Search Report, Written Opinion of the International Searching Authority, and Search History in PCT/US2022/076279, mailed Feb. 2, 2023.

* cited by examiner

EXCLUSION DEVICE COVERS AND RELATED METHODS

CROSS REFERENCE TO RELATED APPLICATIONS

This application claims the benefit of U.S. Provisional Application No. 63/243,313, filed Sep. 13, 2021, U.S. Provisional Application No. 63/243,322, filed Sep. 13, 2021, U.S. Provisional Application No. 63/243,329, filed Sep. 13, 2021, and U.S. Provisional Application No. 63/243,335, filed Sep. 13, 2021, each of which is incorporated by reference herein.

INTRODUCTION

The present disclosure is directed to medical instruments and devices, and, more specifically, to exclusion devices for anatomical structures, and related instruments and related methods.

The present disclosure contemplates that atrial fibrillation is a common heart arrhythmia, affecting millions of people in the United States. In some patients with atrial fibrillation, stagnant blood in the heart's left atrial appendage ("LAA") may be a source of blood clots, which may enter the blood circulation and increase the risk of stroke. Excluding the LAA, which may create electrical and/or fluidic isolation of the LAA, may be beneficial in terms of reducing the atrial fibrillation burden and/or reducing the risk of stroke for some patients. Accordingly, in some patients, it may be desirable to exclude the LAA by securely sealing the LAA orifice at the base of the LAA using an occlusion device.

The present disclosure contemplates that some LAA occlusion clips may be relatively large such that they (or the associated applier) may tend to obstruct a surgeon's view, such as the surgeon's view of potentially interfering, nearby structures. Also, some relatively larger LAA occlusion clips may be difficult or impossible to use in connection with minimally invasive surgical approaches. Accordingly, the present disclosure contemplates that, in some circumstances, some users may prefer exclusion devices having relatively smaller profiles.

While known exclusion devices for anatomical structures have been used safely and effectively, the present disclosure contemplates that improvements in the construction and operation of occlusion devices and related instruments and methods may be beneficial for users (e.g., surgeons) and patients. Accordingly, the present disclosure includes various improvements which may enhance the construction, operation, and methods of use of exclusion devices and related instruments and methods.

It is an aspect of the present disclosure to provide an exclusion device for an anatomical structure, including a first beam, a second beam, and/or at least one spring operatively coupled to the first beam and the second beam to exert a closing force on the first beam and the second beam and bias the first beam and the second beam in a closing direction. The at least one spring may be operatively coupled to the first beam by a first crimp connection.

In a detailed embodiment, the first crimp connection may include a plastically deformed portion of the at least one spring engaged with a plastically deformed portion of the first beam. The spring may be generally U-shaped and/or may include a first end portion and/or a second end portion generally opposite from a connecting portion.

In a detailed embodiment, the first beam may include a spring cavity receiving the first end portion of the spring. The spring cavity may be oriented generally longitudinally within the first beam.

In a detailed embodiment, the first beam may include a spring stress reduction feature proximate the first cavity. The spring stress reduction feature may include an outwardly facing, rounded spring contact surface configured to reduce stress concentrations in the spring when the first beam is separated from the second beam.

In a detailed embodiment, the first beam may include an outer wall generally opposite a clamping surface. The clamping surface may generally face the second beam. The outer wall may include an outwardly facing recess proximate the cavity. The outwardly facing recess may be configured to receive a tool therein for crimping the first beam and the spring. A thickness of the outer wall proximate the outwardly facing recess may be less than a thickness of the outer wall adjacent to the outwardly facing recess.

In a detailed embodiment, the first beam may include an inner wall generally disposed towards a clamping surface. The clamping surface may generally face the second beam. The inner wall may include a cavity recess within the spring cavity. At least a portion of the first end portion of the spring may at least partially occupy the cavity recess. The cavity recess may be generally in the form of partial sphere. The cavity recess may include a through hole.

In a detailed embodiment, the first beam may include a longitudinal slot between the spring cavity and an end of the first beam. At least a portion of the spring may be slidably received within the slot. The slot may be configured to cooperate with the spring to reduce the likelihood of the first beam and the second beam from moving out of a generally coplanar alignment.

In a detailed embodiment, the at least one spring may be operatively coupled to the second beam by a second crimp connection. The at least one spring may include a first spring and a second spring. The first spring may be operatively coupled to the first beam by the first crimp connection and/or may be operatively coupled to the second beam by the second crimp connection. The second spring may be operatively coupled to the first beam by a third crimp connection and/or to the second beam by a fourth crimp connection.

In a detailed embodiment, at least one of the first beam and the second beam may include a clamping surface including at least one gripping feature.

It is an aspect of the present disclosure to provide a method of making an exclusion device for an anatomical structure, including obtaining a first beam, a second beam, and a first spring. The first beam may include a generally longitudinally oriented spring cavity. The first spring may be generally U-shaped and/or may include a first end portion and/or a second end portion generally opposite from a connecting portion. The method may include inserting the first spring first end portion into the first beam spring cavity. The method may include crimping the first beam and the first spring to secure the first spring first end portion in the first beam spring cavity.

In a detailed embodiment, crimping the first beam and the first spring may include plastically deforming a portion of the first beam and a portion of the first spring.

In a detailed embodiment, obtaining the first beam may include at least one of 3D printing the first beam, metal injection molding the first beam, and/or machining the first beam.

In a detailed embodiment, inserting the first spring first end portion into the first beam spring cavity may include positioning the first spring first end portion through a generally longitudinal slot between the spring cavity and an end of the first beam. The slot is configured to prevent rotation of the first spring about the first end portion of the first spring.

In a detailed embodiment, the first beam may include an outer wall at least partially defining the spring cavity. The outer wall may include an outwardly facing recess. Crimping the first beam and the first spring may include receiving a tool at least partially within the outwardly facing recess of the outer wall. The outer wall may be disposed generally opposite a clamping surface of the first beam.

In a detailed embodiment, the first beam may include an inner wall at least partially defining the spring cavity. The inner wall may include a cavity recess within the spring cavity. Crimping the first beam and the first spring may include deforming at least a portion of the first end portion of the first spring into the cavity recess. The inner wall may be disposed generally towards a clamping surface of the first beam.

In a detailed embodiment, the method may include obtaining a second spring. The second spring being generally U-shaped. The method may include crimping the second beam and the first spring to secure the first spring to the second beam. The method may include crimping the first beam and the second spring to secure the second spring the first beam. The method may include crimping the second beam and the second spring to secure the second spring to the second beam.

It is an aspect of the present disclosure to provide a method of occluding an anatomical structure, including delivering an exclusion device to a surgical site in a closed configuration. The exclusion device may include a first beam, a second beam, at least one spring operatively coupled to the first beam and/or the second beam to exert a closing force on the first beam and/or the second beam. The at least one spring may be operatively coupled to the first beam by a crimp connection. The method may include reconfiguring the exclusion device from the closed configuration to an open configuration. The method may include positioning the exclusion device around an anatomical structure. The method may include reconfiguring the exclusion device into the closed configuration to at least partially occlude the anatomical structure, which may include reconfiguring the exclusion device into the closed configuration using the closing force exerted by the at least one spring.

In a detailed embodiment, reconfiguring the exclusion device into the closed configuration may include allowing the closing force exerted by the at least one spring to move the first beam and the second beam into the closed configuration.

In a detailed embodiment, the method may include detaching the exclusion device from an application instrument, withdrawing the application instrument, and/or maintaining the exclusion device in the closed configuration using the at least one spring.

In a detailed embodiment, the exclusion device may include a left atrial appendage occlusion clip. Positioning the exclusion device around the anatomical structure may include positioning the left atrial appendage occlusion clip around a left atrial appendage. At least partially occluding the anatomical structure may include at least partially occluding the left atrial appendage.

It is an aspect of the present disclosure to provide an exclusion device for an anatomical structure, including a first beam, a second beam, and a first spring operatively coupled to the first beam and the second beam to exert a closing force on the first beam and the second beam. The first spring may be generally U-shaped and/or may include a first end portion and a second end portion generally opposite a connecting portion.

In a detailed embodiment, the spring may include a first reverse bend portion between the connecting portion and the first end portion. The spring may include a second reverse bend portion between the connection portion and the second end portion. The first beam, the second beam, and/or the first spring may be configured so that a closed bias pre-load is provided by the first reverse bend portion and/or the second reverse bend portion.

In a detailed embodiment, between the connecting portion and the first reverse bend portion and the second reverse bend portion, the first spring may be generally converging. Between the first reverse bend portion and the first end portion, and between the second reverse bend portion and the second end portion, the spring may be generally diverging. In a detailed embodiment, the spring may be substantially coplanar.

In a detailed embodiment, the closing force may vary with a temperature of the first spring. The first spring may be constructed from at least one of Nitinol, stainless steel, or a polymer, or any other suitable biocompatible elastic material.

In a detailed embodiment, the first end portion of the first spring may be operatively coupled to the first beam by a first pivot. The first pivot may be rotatable relative to the first beam. The second end portion of the second spring may be operatively coupled to the second beam by a second pivot. The second pivot may be rotatable relative to the second beam.

In a detailed embodiment, the first spring may be rigidly coupled to at least one of the first beam and the second beam. The first spring may be configured to exert the closing force by bending and/or torsional loads.

It is an aspect of the present disclosure to provide a method of making an exclusion device for an anatomical structure, including operatively connecting a first spring between a first beam and a second beam to exert a closing force on the first beam and the second beam. The first spring may be generally U-shaped and/or may include a respective first end portion and a respective second end portion generally opposite a connecting portion.

In a detailed embodiment, the method may further include operatively connecting a second spring between the first beam and the second beam to exert the closing force on the first beam and the second beam. The second spring may be generally U-shaped and/or may include a respective first end portion and a respective second end portion generally opposite a respective connecting portion.

In a detailed embodiment, operatively connecting the first spring between the first beam and the second beam may include pivotably coupling the first end portion of the first spring to the first beam and/or pivotably coupling the second end portion of the first spring to the second beam.

It is an aspect of the present disclosure to provide a method of occluding an anatomical structure, including delivering an exclusion device to a surgical site in a closed configuration. The exclusion device may include a first beam, a second beam, and/or a first spring operatively coupled to the first beam and the second beam to exert a closing force on the first beam and the second beam. The first spring may be generally U-shaped and/or may include a first end portion and a second end portion generally opposite a connecting portion. The first spring may include a first reverse bend portion between the connecting portion and the first end portion and/or a second reverse bend portion between the connecting portion and the second end portion. The method may include reconfiguring the exclusion device from the closed configuration to an open configuration. The method may include positioning the exclusion device around an anatomical structure. The method may include reconfiguring the exclusion device into the closed configuration to at least partially occlude the anatomical structure.

In a detailed embodiment, the method may further include detaching the exclusion device from an application instrument, withdrawing the application instrument, and/or maintaining the exclusion device in the closed configuration using the first spring. The closing force exerted by the first spring may vary with a temperature of the first spring. The method may include increasing the closing force exerted by the first spring by increasing the temperature of the first spring.

In a detailed embodiment, the exclusion device may include a left atrial appendage occlusion clip. Positioning the exclusion device around the anatomical structure may include positioning the left atrial appendage occlusion clip around a left atrial appendage. At least partially occluding the anatomical structure may include at least partially occluding the left atrial appendage.

It is an aspect of the present disclosure to provide an exclusion device, including a first clamping portion; a second clamping portion opposing the first clamping portion; and/or a biocompatible fabric cover at least partially sheathing at least one of the first clamping portion and the second clamping portion. The cover may be generally tubular and/or may define a relaxed circumference when the first clamping portion and the second clamping portion are in a closed configuration. At least a portion of the cover may be configured to stretch to a stretched circumference of about 2× to about 3× the relaxed circumference when the first clamping portion and the second clamping portion are reconfigured from the closed configuration to an open configuration.

In a detailed embodiment, the exclusion device may include a closed-biased left atrial appendage occlusion clip. The cover may be configured to promote tissue ingrowth. The cover may include a circular knit warp weave fabric. The cover may include woven polyethylene terephthalate yarn. The cover may include at least one weld securing the cover on the at least one of the first clamping portion and the second clamping portion. The at least one weld may include at least one ultrasonic weld. The at least one weld may include at least one heat weld. The at least one weld may be configured and/or arranged to facilitate tissue ingrowth into the cover near the at least one weld.

It is an aspect of the present disclosure to provide a method of making an exclusion device for an anatomical structure. The method may include assembling a clamping portion of an exclusion device comprising a beam and a biocompatible fabric cover and/or securing the cover on the beam by ultrasonic welding a first portion of the cover to a second portion of the cover.

In a detailed embodiment, the ultrasonic welding operation may include overlapping the first portion of the cover and the second portion of the cover and/or applying ultrasonic energy to the overlapped first portion of the cover and the second portion of the cover to create at least one ultrasonic weld configured and arranged to facilitate tissue ingrowth into the cover proximate the at least one ultrasonic weld. Overlapping the first portion of the cover and the second portion of the cover may include positioning the second portion of the cover generally radially within the first portion of the cover. Applying ultrasonic energy to the overlapped first portion of the cover and the second portion of the cover may include applying ultrasonic energy at about 40 kHz.

It is an aspect of the present disclosure to provide a method of making an exclusion device for an anatomical structure. The method may include assembling a clamping portion of an exclusion device comprising a beam and a biocompatible fabric cover and/or securing the cover on the beam by heat welding a first portion of the cover to a second portion of the cover.

In a detailed embodiment, the heat welding operation may include overlapping the first portion of the cover and the second portion of the cover and/or applying heat to the overlapped first portion of the cover and the second portion of the cover to create at least one heat weld configured and arranged to facilitate tissue ingrowth into the cover proximate the at least one heat weld. The heat welding operation may include positioning a protective sheet between a heat source and the cover and/or applying heat to the first portion of the cover and the second portion of the cover through the protective sheet using the heat source. The protective sheet may include polytetrafluoroethylene.

It is an aspect of the present disclosure to provide a method of occluding an anatomical structure. The method may include delivering an exclusion device to a surgical site in a closed configuration and/or reconfiguring the exclusion device from the closed configuration to an open configuration. The exclusion device may include a first clamping portion, a second clamping portion, and/or a biocompatible fabric cover at least partially sheathing at least one of the first clamping portion and the second clamping portion. The cover may be generally tubular and/or may define a relaxed circumference when the first clamping portion and the second clamping portion are in the closed configuration. Reconfiguring the exclusion device from the closed configuration to the open configuration may include stretching at least a portion of the cover to a stretched circumference of about 2× to about 3× of the relaxed circumference.

In a detailed embodiment, the exclusion device may include at least one spring operatively coupled to the first clamping portion and the second clamping portion to exert a closing force on the first clamping portion and the second clamping portion. The method may further include positioning the exclusion device around an anatomical structure and/or at least partially occluding the anatomical structure by reconfiguring the exclusion device into the closed configuration using the closing force exerted by the at least one spring. The exclusion device may include a left atrial appendage occlusion clip. Positioning the exclusion device around the anatomical structure may include positioning the left atrial appendage occlusion clip around a left atrial appendage. At least partially occluding the anatomical structure may include at least partially occluding the left atrial appendage.

It is an aspect of the present disclosure to provide a biocompatible cover for an exclusion device that stretches about 2× to about 3× its original circumference. It is an aspect of the present disclosure to provide a biocompatible cover for an exclusion device including at least one ultrasonic weld securing the cover on the exclusion device. It is an aspect of the present disclosure to provide a biocompatible cover for an exclusion device including at least one heat weld securing the cover on the exclusion device. It is an aspect of the present disclosure to provide a biocompatible cover for an exclusion device that is configured to promote tissue ingrowth. It is an aspect of the present disclosure to provide a left atrial appendage occlusion clip. It is an aspect of the present disclosure to provide a cover for an exclusion device including a circular knit warp weave fabric.

It is an aspect of the present disclosure to provide an application instrument for an exclusion device for an anatomical structure including an end effector including a head configured to be disposed distally on a shaft, a stationary jaw fixedly disposed on the head and configured to releasably couple to a first clamping portion of an exclusion device for an anatomical structure, the exclusion device being biased in a closing direction, and a movable jaw movably disposed on the head and configured to releasably couple to a second clamping portion of the exclusion device. The movable jaw may be movable relative to the stationary jaw to reconfigure the exclusion device from a closed configuration to an open configuration. The movable jaw is oriented generally parallel to the stationary jaw when the exclusion device is in the open configuration and the closed configuration.

In a detailed embodiment, the exclusion device may include at least one spring arranged to exert a closing force on the first clamping portion and the second clamping portion. The end effector may be configured to facilitate reconfiguration of the exclusion device from the open configuration to the closed configuration using the closing force exerted by the at least one spring.

In a detailed embodiment, the application instrument may include the shaft, and the head may be disposed distally on the shaft. The application instrument may further include a handle portion disposed proximally on the shaft. The handle portion may include a first actuator operable by a user to reconfigure the exclusion device from the closed configuration to the open configuration. The handle portion may include a second actuator operable by a user to deploy the exclusion device from the first jaw and the second jaw. The second actuator may be operatively coupled to the end effector by a deployment cable. The end effector may include a cable management element arranged to allow movement of the movable jaw without relative movement of the deployment cable. The cable management element may include a cable management pin.

In a detailed embodiment, the end effector may include a cover secured to the head. The cover may be secured to the head by at least one of a rivet, an orbital rivet, a weld, or a threaded fastener.

In a detailed embodiment, the movable jaw may be disposed on a traveler. The traveler may be movably disposed on the head. The end effector may include at least one friction reduction element operatively interposing the traveler and the head. The at least one friction reduction element may include at least one ball bearing, at least one roller, or at least one low-friction slider.

It is an aspect of the present disclosure to provide a method of making an application instrument for an exclusion device for an anatomical structure, including assembling an end effector. The end effector may include a head configured to be disposed distally on a shaft, a stationary jaw fixedly disposed on the head and configured to releasably couple to a first clamping portion of an exclusion device for an anatomical structure, the exclusion device being biased in a closing direction, and/or a movable jaw movably disposed on the head and configured to releasably couple to a second clamping portion of the exclusion device, the movable jaw remaining generally parallel to the stationary jaw when the exclusion device is in the open configuration and the closed configuration. The method may include coupling the end effector distally on the shaft. The method may include coupling a handle portion proximally on the shaft.

In a detailed embodiment, the method may further include operatively connecting a first actuator on the handle portion to the end effector so that the first actuator is operative to move the movable jaw to reconfigure the exclusion device from the closed configuration to the open configuration. The method may further include operatively connecting a second actuator on the handle portion to the end effector so that the second actuator is operative to deploy the exclusion device from the first jaw and the second jaw. Operatively connecting the second actuator on the handle portion to the end effector may include routing a deployment cable around at least one cable management element configured to allow movement of the movable jaw without relative movement of the deployment cable.

In a detailed embodiment, assembling an end effector may include attaching a cover to the head. Attaching the cover to the head may include riveting the cover to the head.

It is an aspect of the present disclosure to provide a method of using an application instrument for an exclusion device for an anatomical structure, including operating a first actuator on a handle portion of an application instrument carrying an exclusion device to reconfigure the exclusion device into an open configuration; positioning an end effector of the application instrument to locate the exclusion device on an anatomical structure; operating the first actuator to reconfigure the exclusion device into a closed configuration on the anatomical structure; and/or operating a second actuator on a handle portion of the application instrument to deploy the exclusion device from the end effector. The end effector may include a head configured to be disposed distally on a shaft, a stationary jaw fixedly disposed on the head and configured to releasably couple to a first clamping portion of the exclusion device, the exclusion device being biased in a closing direction, and/or a movable jaw movably disposed on the head and configured to releasably couple to a second clamping portion of the exclusion device. Operating the first actuator on the handle portion of the application instrument carrying the exclusion device to reconfigure the exclusion device into the open configuration may include moving the movable jaw relative to the stationary jaw to reconfigure the exclusion device from the closed configuration to the open configuration while the movable jaw and the stationary jaw are oriented generally in parallel.

In a detailed embodiment, operating the second actuator on the handle portion of the application instrument to deploy the exclusion device from the end effector may include moving a deployment cable around at least one cable management element configured to allow movement of the movable jaw without relative movement of the deployment cable.

It is an aspect of the present disclosure to provide any method, process, apparatus, or system comprising one or more elements described herein. It is as aspect of the present disclosure to provide any combination of any one or more elements described herein.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical devices and procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of this disclosure. However, for clarity and precision, the example embodiments as discussed below may include optional steps, methods, and features that one of ordinary skill should recognize as not being a requisite to fall within the scope of the present disclosure.

The present disclosure includes, among other things, medical instruments and devices, and, more specifically, exclusion devices for anatomical structures, and related instruments and related methods. Some example embodiments according to at least some aspects of the present disclosure may be useful as left atrial appendage occlusion clips for exclusion of a patient's left atrial appendage, such as to reduce the patient's atrial fibrillation burden and/or to reduce the patient's risk of stroke. It is to be understood, however, that various example embodiments according to the present disclosure may be utilized in connection with anatomical structures other than left atrial appendages. The following description begins with an overview of an example exclusion device and application instrument, followed by detailed descriptions of specific aspects of various example embodiments.

Generally, some example exclusion devices according to at least some aspects of the present disclosure may be delivered to a surgical site in a closed configuration using an application instrument. The application instrument may be actuated to reconfigure the exclusion device into an open configuration. The application instrument may be manipulated to position the exclusion device around an anatomical structure. The application instrument may be actuated to reconfigure the exclusion device into a closed configuration to at least partially occlude the anatomical structure. The application instrument may be actuated to detach the exclusion device, and the application instrument may be withdrawn from the surgical site.

Figure 1:
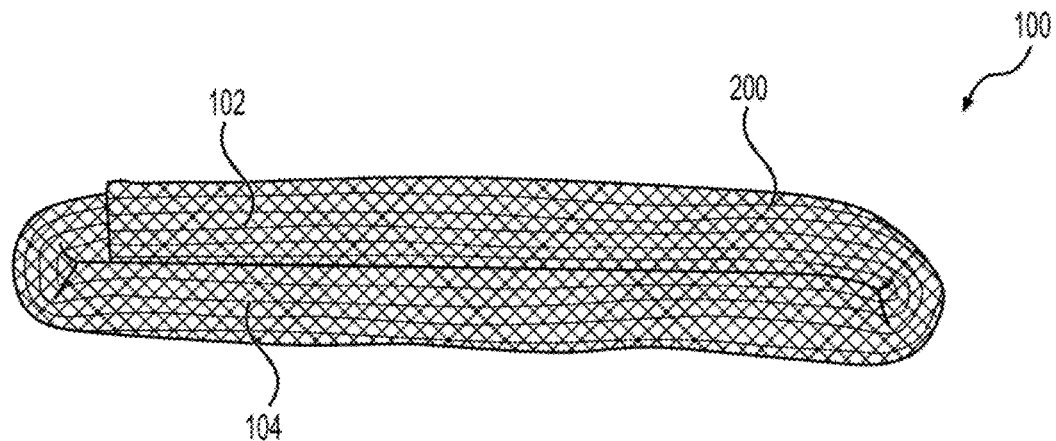
FIG. 1 is an elevation view of an example exclusion device for an anatomical structure in a closed configuration.

FIG. 1 is an elevation view of an example exclusion device 100 for an anatomical structure in a closed configuration, in accordance with at least some aspects of the present disclosure. This example exclusion device 100 is generally in the form of an occlusion clip including a first clamping portion 102 and an opposing second clamping portion 104. The first clamping portion 102 and the second clamping portion 104 are biased in a closing direction (e.g., generally towards each other).

The illustrated exclusion device 100 includes a cover 200, which at least partially sheaths one or both of the clamping portions 102, 104. This example cover 200 is constructed from a textile, which may initiate the body's healing response and/or promote tissue ingrowth. In the illustrated embodiment, the cover 200 is generally tubular and covers each of the clamping portions 102, 104 individually in a generally toroidal manner. In some example embodiments, the cover 200 may substantially enclose the other components of the exclusion device 100.

Some example exclusion devices 100 according to at least some aspects of the present disclosure may be configured so that, in the closed configuration, the exclusion device 100 envelope may be less than about 5 mm laterally. Accordingly, some example embodiments may be configured to fit through relatively small ports, such as a 5 mm trocar. The present disclosure contemplates that some other implantable exclusion devices may have a device envelop that is about 12 mm laterally. See, for example, some devices described in U.S. Pat. No. 10,166,024, issued Jan. 1, 2019, which is incorporated by reference. Accordingly, some example exclusion devices 100 according to at least some aspects of the present disclosure may be advantageous when used in connection with minimally invasive surgical approaches. Additionally, some example exclusion devices 100 according to at least some aspects of the present disclosure may tend to obstruct a surgeon's view to a lesser extent than relatively larger exclusion devices, thus allowing the surgeon to better visualize nearby structures, such as nearby structures which might potentially interfere with a procedure.

Figure 2:
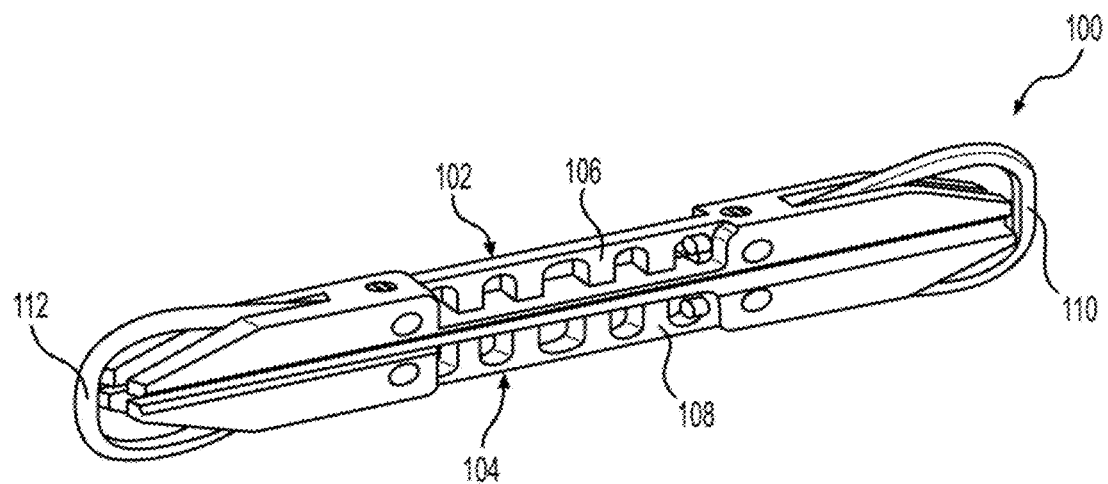
FIG. 2 is a perspective view of the exclusion device of FIG. 1 in the closed configuration and without a cover.
Figure 3:
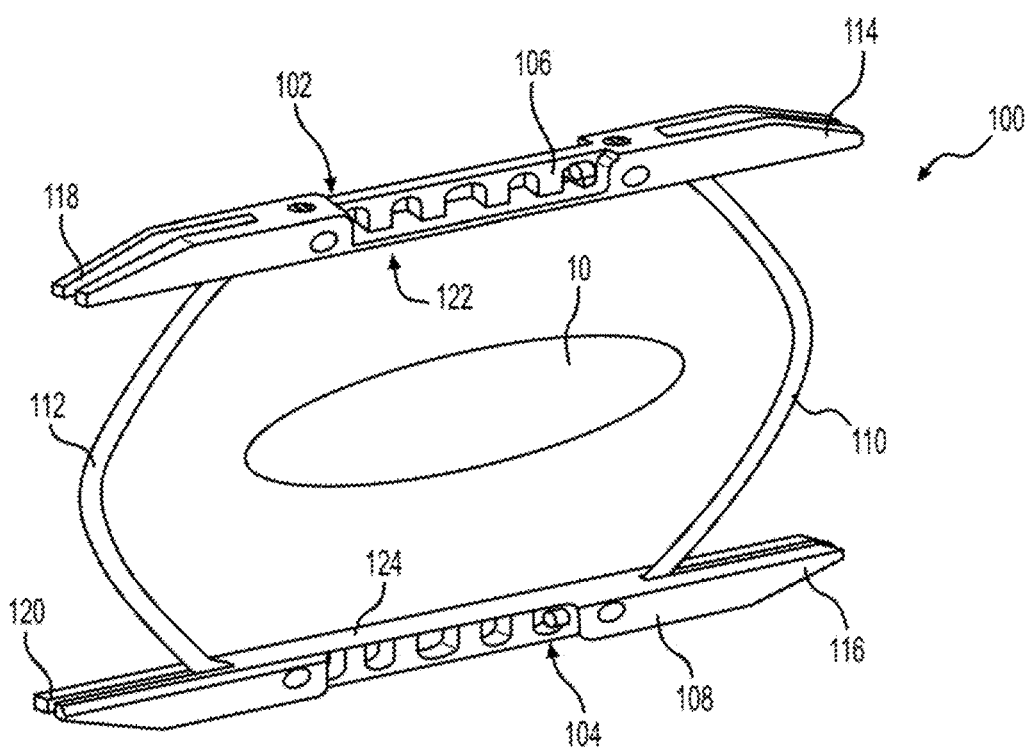
FIG. 3 is a perspective view of the exclusion device of FIG. 1 in an open configuration and without the cover.

FIG. 2 is a perspective view of the exclusion device 100 of FIG. 1 in the closed configuration and without the cover 200, and FIG. 3 is a perspective view of the exclusion device 100 of FIG. 1 in the open configuration and without the cover 200, all in accordance with at least some aspects of the present disclosure. Referring to FIGS. 1-3, in this example exclusion device 100, the first clamping portion 102 includes a first beam 106 and the second clamping portion 104 includes a second beam 108. The first beam 106 and the second beam 108 are coupled together by a generally U-shaped first spring 110 and a generally U-shaped second spring 112. Generally, the first spring 110 is coupled to the beams 106, 108 inward from their respective first ends 114, 116. Similarly, the second spring 112 is coupled to the beams 106, 108 inward from their respective second ends 118, 120.

In this example embodiment, the beams 106, 108 include opposed clamping surfaces 122, 124, which are configured to engage an anatomical structure 10 positioned therebetween. For example, the exclusion device 100 may be positioned to at least partially occlude an anatomical structure 10 including a left atrial appendage by clamping the LAA between the clamping surfaces 122, 124 of the clamping portions 102, 104. Some embodiments may be configured to accommodate LAAs from about 24 mm to about 50 mm wide, for example.

In the illustrated embodiment, the springs 110, 112 are arranged to bias the first beam 106 and the second beam 108 towards each other (e.g., in a closing direction). In this embodiment, the first clamping portion 102 and the second clamping portion 104 are substantially in contact in the closed configuration when the exclusion device 100 is empty. Specifically, the clamping surfaces 122, 124 (which may be covered by the cover 200) may be substantially in contact with one another in the closed configuration when the exclusion device 100 is empty. Some alternative example embodiments may be configured so that the springs 110, 112 bias the beams 106, 108 in the closing direction but do not draw the clamping portions fully into contact with each other in the closed configuration when the exclusion device 100 is empty. Thus, in some such embodiments, even with no other structure interposing the clamping portions 102, 104, a gap may exist between the clamping portions 102, 104 in the closed configuration. As used herein, "closed configuration" may refer to a configuration in which an exclusion device 100 is substantially independently maintaining its clamping portions 102, 104 in a configuration closer together than the fully open configuration, whether or not the clamping portions are in contact with each other and whether or not any other object (e.g., anatomical structure) interposes the clamping portions. In the illustrated embodiment, in the fully open configuration, the beams 106, 108 are spaced apart about 14 mm.

In the illustrated embodiment, the springs 110, 112 are selected so that the clamping portions 102, 104 are spaced apart when in the closed configuration with an anatomical structure 10 interposing the clamping surfaces 122, 124. As a result, the anatomical structure 10 may be substantially occluded, but is generally not severed.

Figure 4:
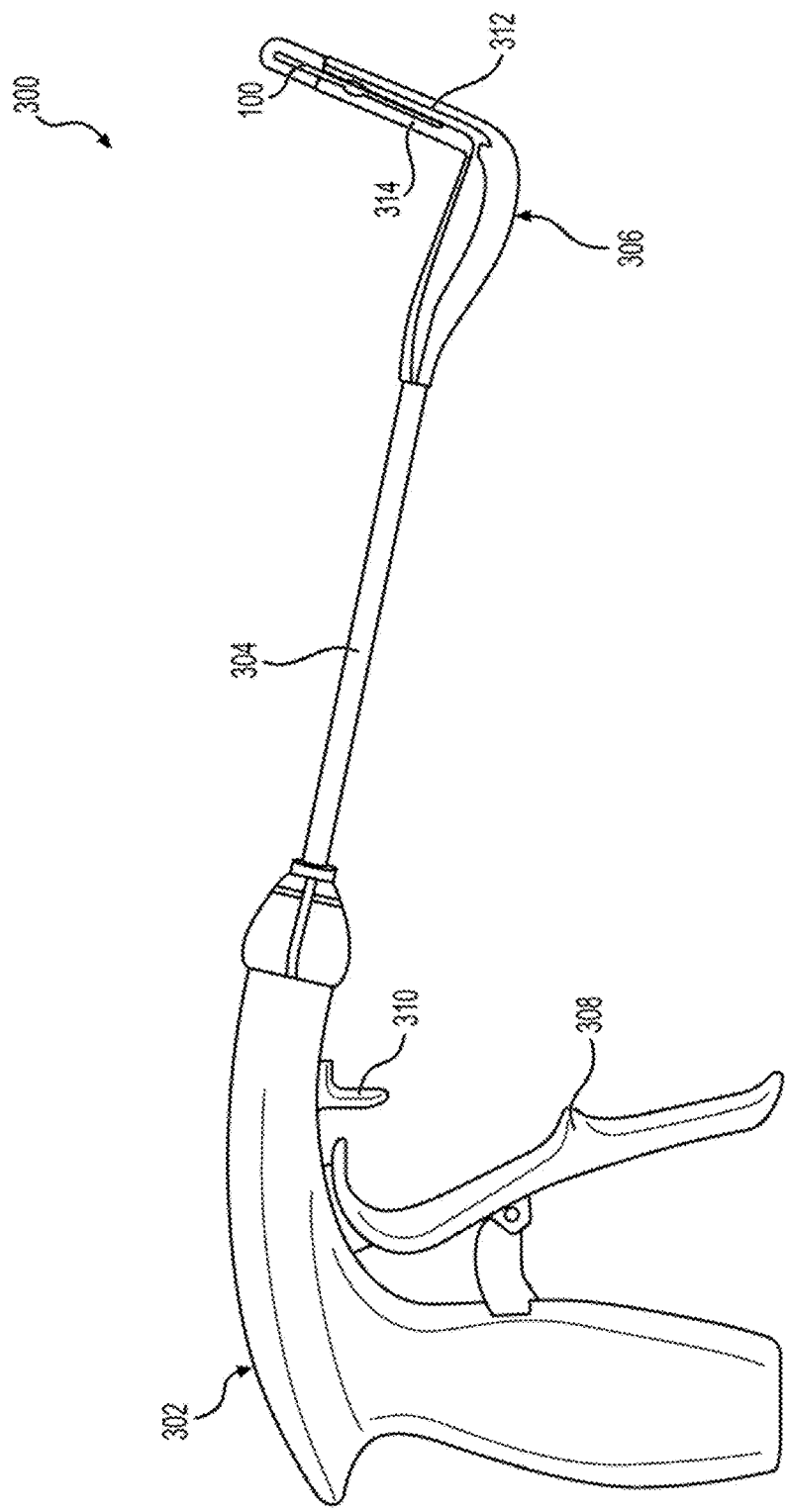
FIG. 4 is an elevation view of an example exclusion device application instrument with the exclusion device of FIG. 1 in a closed configuration.
Figure 5:
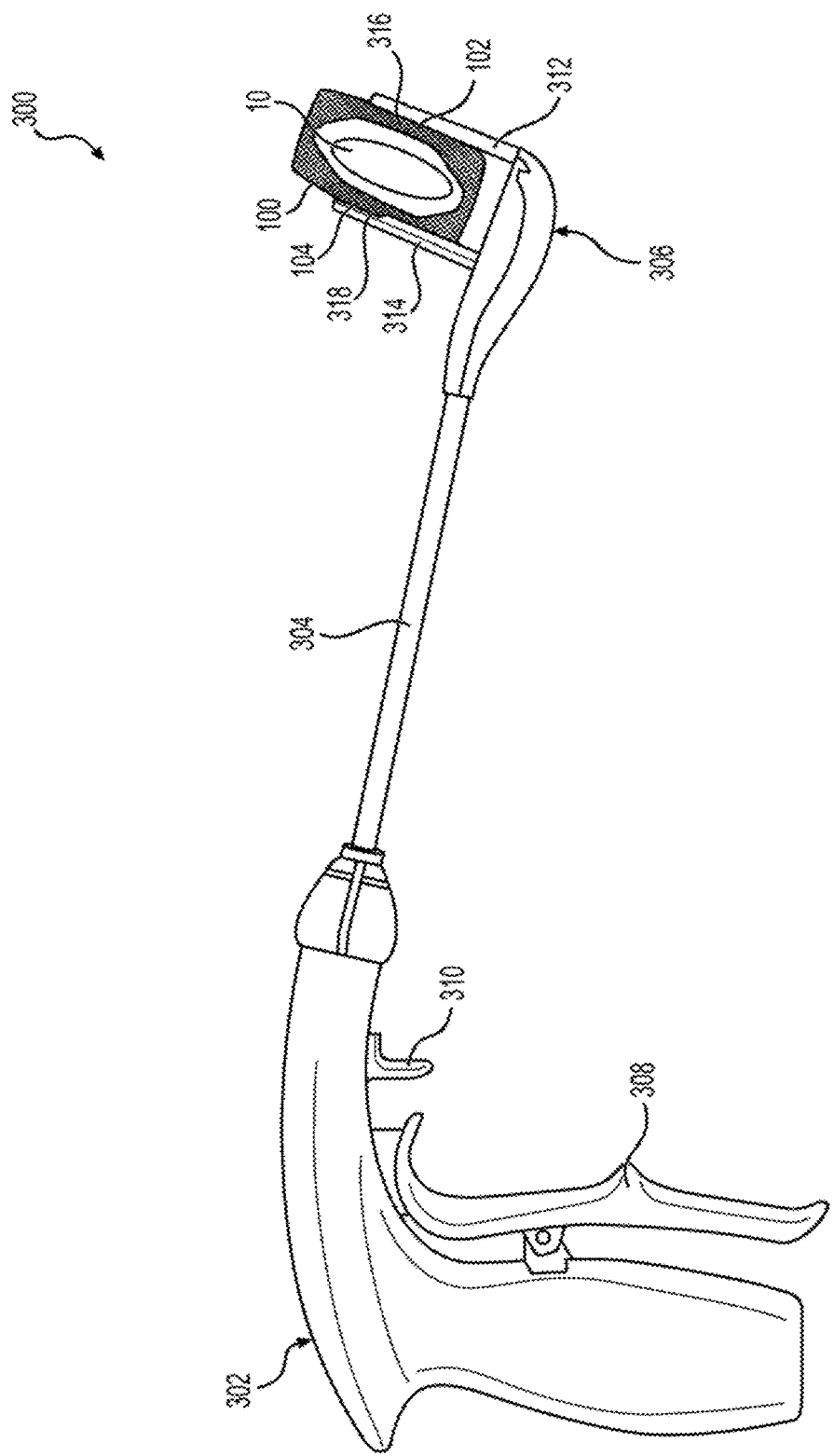
FIG. 5 is an elevation view of the example exclusion device application instrument of FIG. 4 with the exclusion device of FIG. 1 in an open configuration.

FIG. 4 is an elevation view of an example exclusion device 100 application instrument 300 with the exclusion device 100 of FIG. 1 in a closed configuration and FIG. 5 is an elevation view of the example exclusion device 100 application instrument 300 of FIG. 4 with the exclusion device 100 of FIG. 1 in an open configuration, all in accordance with at least some aspects of the present disclosure. This example application instrument 300 includes a generally proximal handle portion 302, an elongated, malleable shaft 304 extending distally from the handle portion 302, and an end effector 306 disposed distally on the shaft 304. As used herein, "distal" may refer to a direction generally away from an operator of a system or device (e.g., a surgeon), such as toward the distant-most end of a device that may be inserted into a patient's body. As used herein, "proximal" may refer to a direction generally toward an operator of a system or device (e.g., a surgeon), such as away from the distant-most end of a device that may be inserted into a patient's body.

In the illustrated embodiment, the exclusion device 100 is releasably secured to the end effector 306 application instrument 300. The end effector 306 is arranged to reconfigure the exclusion device 100 between open and closed configurations and to release the exclusion device 100 based on operation of one or more actuators 308, 310 on the handle portion 302 by the user. For example, the handle portion 302 and/or the actuators 308, 310 may be generally similar in construction and operation to those described in U.S. Patent Application Publication No. 2019/0142428, published on May 16, 2019, which is incorporated by reference herein in its entirety.

In the illustrated embodiment, the end effector 306 includes a distal, stationary jaw 312 and a proximal, movable jaw 314. Each of the clamping portions 102, 104 of the exclusion device 100 is releasably coupled to a respective one of the jaws 312, 314. Operation of the first actuator 308 causes the end effector 306 to reconfigure the exclusion device 100 between the open and closed configurations by moving the movable jaw 314 away from and towards the stationary jaw 312. In some example embodiments, the first actuator 308 may be operable to open the exclusion device 100, and the closing-biased nature of the exclusion device 100 may be operative to close the exclusion device 100 as the first actuator 308 is released by the user. In some example embodiments, the end effector 306 may be configured for substantially parallel opening of the first clamping portion 102 and second clamping portion 104 of the exclusion device 100. Operation of the second actuator 310 may cause the end effector 306 to release (e.g., deploy) the exclusion device 100 by detaching the clamping portions 102, 104 from the jaws 312, 314. For example, the clamping portions 102, 104 may be releasably secured to the respective jaws 312, 314 by respective sutures 316, 318, which may be released by operation of the second actuator 310. Example mechanisms arranged to deploy an exclusion device from an end effector are described in U.S. Patent Application Publication No. 2018/0036007, published Feb. 8, 2018, which is incorporated by reference. In some example embodiments, the sutures 316, 318 (or other attachment elements) may be positioned generally centered longitudinally along the clamping portions 102, 104. The actuators 308, 310 may be operatively coupled to the end effector 306 by one or more mechanical linkages, such as one or more rods and/or cables.

The present disclosure contemplates that covers for implantable exclusion devices may promote tissue ingrowth and/or may provide barriers between relatively hard components of the devices (e.g., beams) and adjacent tissues (e.g., the heart). Some implantable exclusion devices may be configured so that the cover generally does not move relative to the structural components. That is, the cover may remain substantially in place on the structural components and/or may not stretch as the exclusion device is reconfigured. Other implantable exclusion devices, such as the exclusion device 100, may include biocompatible covers 200 that are configured to move (e.g., stretch) relative to underlying components.

Figure 6:
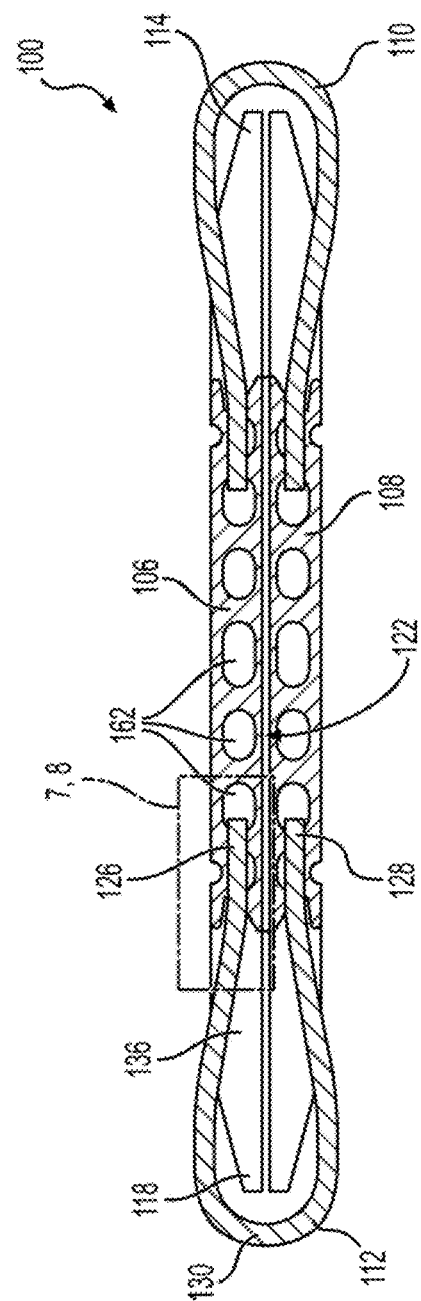
FIG. 6 is a longitudinal cross section view of the exclusion device of FIG. 1 in the closed configuration and without the cover.
Figure 7:
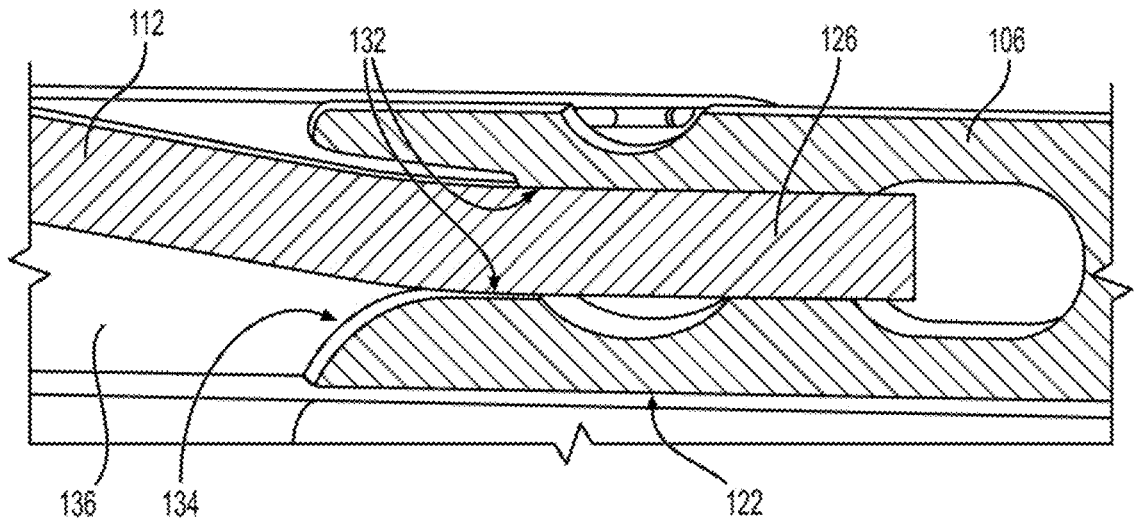
FIG. 7 is a detailed longitudinal cross section view of a portion of a first beam proximate a second end.
Figure 8:
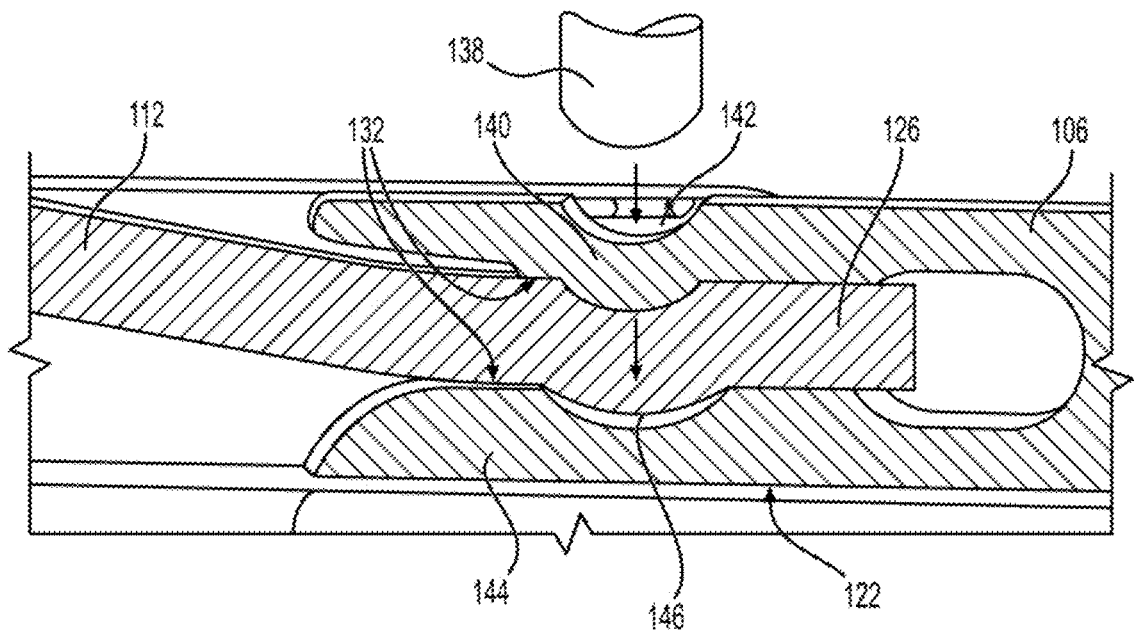
FIG. 8 is a detailed longitudinal cross section view of a portion of a first beam proximate a second end.

FIG. 6 is a longitudinal cross section view of the exclusion device 100 of FIG. 1 in the closed configuration and without the cover 200, and FIGS. 7 and 8 are detailed longitudinal cross section views of a portion of the first beam 106 proximate the second end 118, all in accordance with at least some aspects of the present disclosure. The following description focuses generally on features of the first beam 106 proximate its second end 118. However, it is to be understood that the first end 114 of the first beam 106 may be substantially similar (e.g., in a mirror-image manner) to the second end 118. Further, the second beam 108 may be substantially similar (e.g., in an inverted manner) to the first beam 106. Accordingly, the description of features of the first beam 106 proximate its second end 118 may apply to other portions of the example exclusion device 100, but is not repeated for brevity.

Referring to FIGS. 2, 3, and 6-8, in the illustrated embodiment, the second spring 112 is generally U-shaped and includes a first end portion 126 and a second end portion 128 generally opposite a connecting portion 130. At least a portion of the first end portion 126 is received within a generally longitudinally oriented spring cavity 132 formed in the first beam 106. The spring cavity 132 is open towards the second end 118 of the first beam 106 and receives the first end portion 126 of the second spring 112 from that direction.

Referring to FIGS. 2, 3, and 7, in the illustrated embodiment, when the exclusion device 100 is reconfigured from the closed position (FIGS. 2 and 7) to the open configuration (FIG. 3), the first end portion 126 of the second spring 112 remains secured within the cavity 132 of the first beam 106. The portion of the second spring 112 proximate the cavity 132 bends from a generally longitudinal, slightly outward orientation (FIGS. 2 and 7) to a markedly inward orientation (FIG. 3). In some example embodiments, the first beam 106 may include a spring stress reduction feature proximate the cavity 132. For example, in the illustrated embodiment, the beam 106 includes an outwardly facing, rounded spring contact surface 134 configured to reduce stress concentrations in the second spring 112 when the exclusion device 100 is in the open configuration. In some example embodiments, the spring contact surface 134 may also facilitate assembly of the exclusion device 100, such as by funneling the first end portion 126 of the second spring 112 into the cavity 132 of the first beam 106.

Referring to FIGS. 2, 3, 6, and 7, in the illustrated embodiment, at least a portion of the beam 106 between the cavity 132 and the second end 118 may include a longitudinal slot 136 extending generally outward from the clamping surface 122. At least a portion of the second spring 112 is slidably received within the slot 136. Generally, the slot 136 may aid in maintaining a generally coplanar alignment of the first beam 106, the second spring 112, and the second beam 108. Accordingly, the second spring 112 and the slot 136 may cooperate to reduce the likelihood of the beams 106, 108 coming substantially out of alignment (e.g., out of plane), such as during opening and/or closing of the exclusion device 100.

Referring to FIGS. 2, 3, 6, and 8, in some example embodiments, the first beam 106 and/or the second spring 112 may be plastically deformed to secure the second spring 112 to the first beam 106. In the illustrated embodiment, a tool such as a punch 138 may be used crimp the beam 106 and the first portion 126 of the second spring 112 to secure them together.

Referring to FIG. 8, in this example embodiment, the outer wall 140 of the first beam 106 (e.g., generally opposite the clamping surface 122) at a crimping location proximate the cavity 132 is thinner than adjacent portions of the beam 106. For example, the outer wall 140 may include an outwardly facing recess 142, which may be configured to receive the punch 138 therein. In some example embodiments, the outwardly facing recess 142 may act as a registration location for the punch 138 and/or may at least partially define the thinner portion of outer wall 140.

Referring still to FIG. 8, in this example embodiment, the inner wall 144 of the first beam 106 (e.g., generally towards the clamping surface 122) may include a cavity recess 146 within the cavity 132. This cavity recess 146 may be generally aligned with the desired crimping motion of the punch 138. In some example embodiments, the cavity recess 146 may provide space to allow deformation of the outer wall 140 of the first beam 106 and/or the first end portion 126 of the second spring 112 past a desired permanent deformation in order to achieve the desired permanent deformation. That is, the cavity recess 146 may provide relief to accommodate elastic deformation of the second spring 112 during the crimping operation, such as due to the relatively high yield strength of the second spring 112 material. In some example embodiments, at least a portion of the first end portion 126 of the second spring 112 may remain at least partially within the cavity recess 146 after the crimping operation. The example cavity recess 146 shown in FIG. 8 is generally in the form of partial sphere, which may be formed, for example, when the first beam 106 is 3D printed. In alternative example embodiments, the cavity recess 146 may have different shapes. For example, the cavity recess 146 may generally have the form of a through hole, such as in a metal injection molded first beam 106.

Generally, during an example crimping operation, the punch 138 may deform at least a portion of the outer wall 140 of the first beam 106 at least partially into the cavity 132, which may deform at least a portion of the first end portion 126 of the second spring 112 at least partially into the recess 146. Depending on the extent of the deformation, the strength of the materials comprising the first beam 106 and the second spring 112, etc., at least a portion of the outer wall 140 of the first beam 106 and/or at least a portion of the first end portion 126 of the second spring 112 may be plastically deformed to form the crimp connection between the first beam 106 and the second spring 112. That is, the crimp connection may include a plastically deformed portion of the second spring 112 engaged with a plastically deformed portion of the first beam 106, for example.

Figure 9:
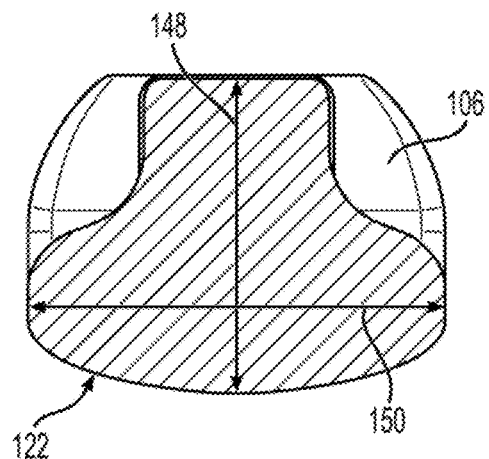
FIG. 9 is a lateral cross section view of an example beam 106 of the exclusion device 100 of FIG. 1.

FIG. 9 is a lateral cross section view of an example beam 106 of the exclusion device 100 of FIG. 1, according to at least some aspects of the present disclosure. In the illustrated embodiment, the beam height 148 is about 2 mm and the beam width 150 is about 2.5 mm. In some example embodiments, the clamping surface 122 may be configured to provide a generally even pressure on the anatomical structure 10 (FIG. 3) across the width of the clamping surface 122. Various clamping surface 122 shapes (e.g., profiles) may be utilized to achieve a desired tradeoff between increasing tissue surface contact area and/or reducing tissue stretching and/or trauma when the exclusion device 100 is closed on the anatomical structure 10. Example curvatures of the clamping surface 122 may include, but are not limited to, curves generally in the form of the curvature of the surface of a water droplet, a natural logarithmic decay curve, a half round shape (e.g., constant radius), oval, parabolic, and/or generally flat.

Figure 10:
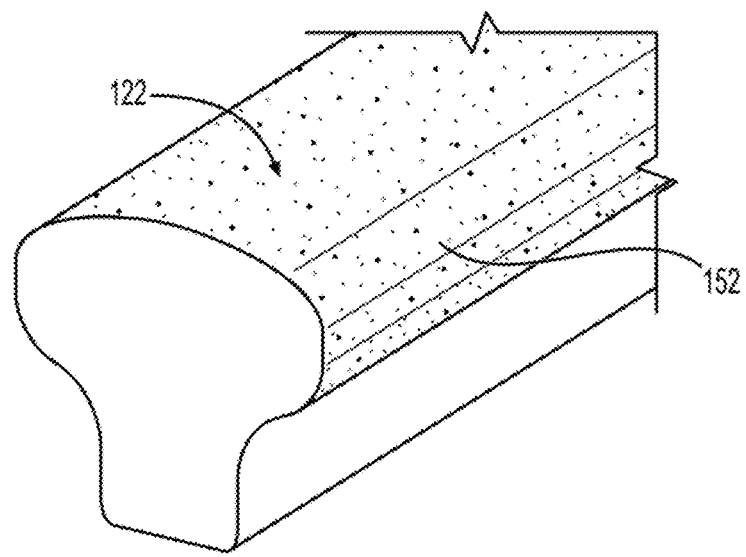
FIG. 10 is a perspective view of an alternative example clamping surface gripping feature.
Figure 11:
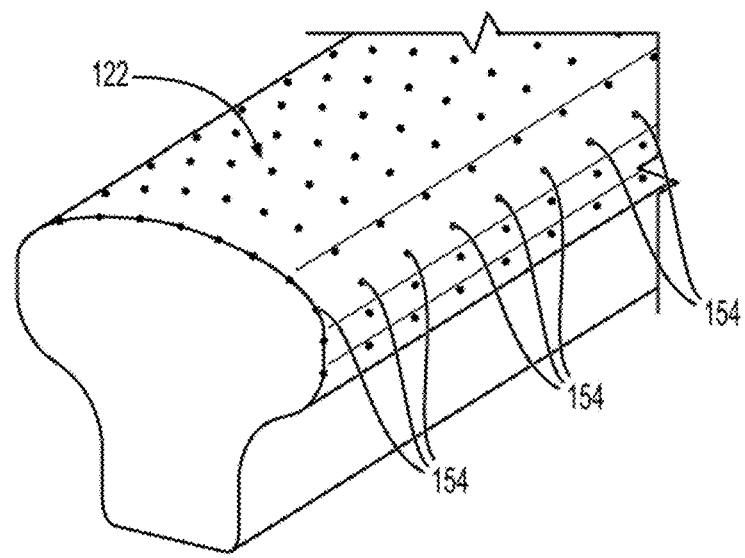
FIG. 11 is a perspective view of an alternative example clamping surface gripping feature.
Figure 12:
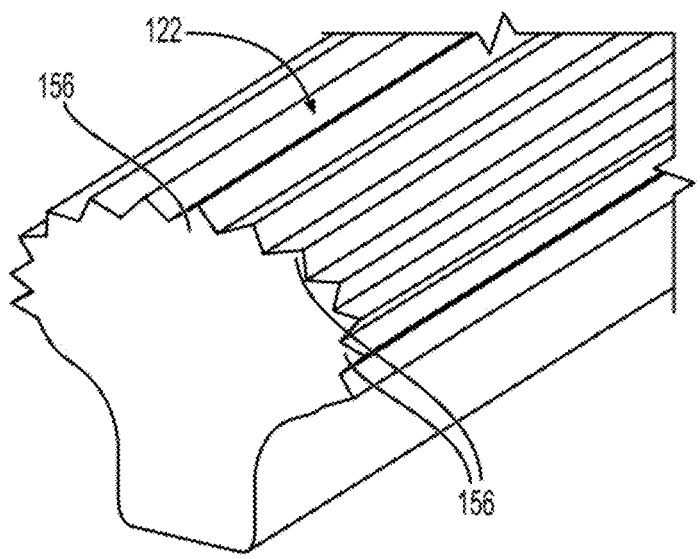
FIG. 12 is a perspective view of an alternative example clamping surface gripping feature.

FIGS. 10-12 are perspective views of alternative example clamping surface 122 gripping features 152, 154, 156, according to at least some aspects of the present disclosure. FIG. 10 illustrates a clamping surface 122 including an example rough surface finish 152. As used herein, "rough surface finish" may refer to a surface that is generally uniformly rough at a fine scale, but which lacks readily individually discernable surface features and/or which presents a generally smooth surface curvature at a larger scale. FIG. 11 illustrates a clamping surface 122 including gripping features comprising protrusions 154. The protrusions 154 may extend generally orthogonally from the clamping surface 122. The protrusions 154 may be generally conically and/or cylindrically shaped, for example. In various example embodiments, the protrusions 154 may be arranged in a regular pattern (e.g., in clusters or lines) and/or generally randomly and/or generally uniformly distributed. For example, a grit media may be embedded generally randomly into the clamping surface 122. In alternative example embodiments, gripping features comprising holes or recesses may be similarly arranged. FIG. 12 illustrates a clamping surface 122 including gripping features comprising ridges 156. In this example embodiment, the ridges 156 are oriented generally longitudinally along the beam 106 (FIG. 2).

Generally, in some example embodiments, the gripping features 152, 154, 156 may be configured to aide in anchoring the exclusion device 100 and cover 200 after the exclusion device is placed on the anatomical structure 10. For example, the gripping features 152, 154, 156 may increase the friction and/or gripping strength between the beams 106, 108 and the cover 200 and/or between the beams 106, 108 and the anatomical structure 10. Accordingly, the gripping features 152, 154, 156 may reduce the likelihood of the cover 200 moving relative to the beams 106, 108 (e.g., circumferentially rolling around the beams 106, 108) and/or may reduce the likelihood of the exclusion device 100 moving relative to the anatomical structure 10. Various gripping features 152, 154, 156 may be formed by 3D printing and/or other manufacturing processes.

Referring to FIGS. 2, 3, 5, 7, and 8, in some example embodiments, the beams 106, 108 may be configured to have sufficient bending strength to allow the exclusion device 100 to be releasably secured to the respective jaws 312, 314 of the end effector 306 of the application instrument 300 using one attachment point for each clamping portion 102, 104. For example, the beams 106, 108 may be configured to have sufficient bending strength to allow the exclusion device 100 to be releasably coupled to the jaws 312, 314 by the individual sutures 316, 318 (or other attachment elements), which may be positioned generally centered longitudinally along the clamping portions 102, 104. In particular, the beams 106, 108 may be designed so that the beam moment of inertia provides sufficient strength and/or limited deflection when subject to generally longitudinally centrally applied opening forces sufficient to overcome the closing forces exerted by the springs 110, 112.

Figure 13:
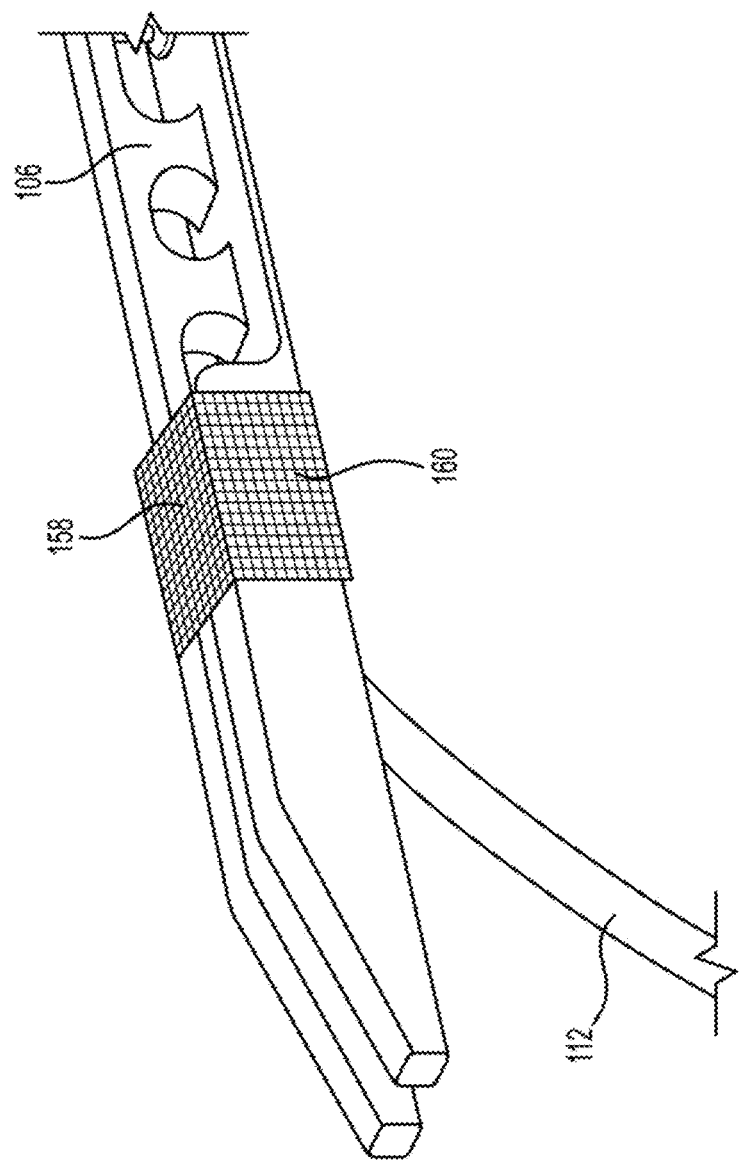
FIG. 13 is a detailed perspective view of a portion of a first beam proximate a second end.

FIG. 13 is a detailed perspective view of a portion of the first beam 106 proximate the second end 118, according to at least some aspects of the present disclosure. Referring to FIGS. 1, 6, 7, and 13, some example beams 106, 108 may include one or more portions configured to act as mandrels for welding operations involving the cover 200. For example, in the illustrated embodiment, the first beam 106 includes outwardly facing surfaces 158, 160, which may be configured to cooperate with externally applied ultrasonic and/or heat welding apparatus for joining portions of the cover 200. In some example embodiments, the outwardly facing surfaces 158, 160 may be generally solid (e.g., without substantial recesses or voids) and/or may be generally flat.

In some example embodiments, the beams 106, 108 may be constructed from one or more metals and/or metal alloys, such as titanium and/or titanium alloys. For example, the beams 106, 108 may be constructed from grade 5 and/or grade 23 titanium. Alternative example embodiments may be constructed of other titanium alloys, such as grade 2. Further alternative example embodiments may be constructed from other materials, such as plastics, stainless steel, magnesium, iron, other titanium grades, nitinol, or other biocompatible materials having desired material properties.

Some example beams 106, 108 may be constructed by 3D printing. Alternative embodiments may be constructed by metal injection molding, chemical etching, and/or stamping. Some example embodiments may be machined.

In some example embodiments, the beams 106, 108 may include features configured to promote tissue in growth after placement of the exclusion device 100. For example, referring to FIG. 6, the beams 106, 108 may include one or more holes or cavities 162 arranged to facilitate tissue in growth. In some example embodiments, the beams 106, 108 may be formed from a generally porous material to facilitate tissue ingrowth. For example, the beams 106, 108 may be 3D printed in a manner that forms them to have a generally porous nature.

Some example methods of making an exclusion device 100 for an anatomical structure 10 according to at least some aspects of the present disclosure may include one or more of the following operations. A first beam 106, a second beam 108, and a first spring 110 may be obtained. Obtaining the first beam 106 may include at least one of 3D printing the first beam 106, metal injection molding the first beam 106, and machining the first beam 106. The first beam 106 may include a generally longitudinally oriented spring cavity 132 and/or the first spring 110 may be generally U-shaped and/or may include a first end portion 126 and a second end portion 126 generally opposite from a connecting portion 130.

In some example embodiments, the first spring 110 first end portion 126 may be inserted into the first beam 106 spring cavity 132. Inserting the first spring 110 first end portion 126 into the first beam 106 spring cavity 132 may include positioning the first spring 110 first end portion 126 through a generally longitudinal slot 136 between the spring cavity 132 and an end 118 of the first beam 106. The slot 136 may be configured to cooperate with the spring 110 to reduce the likelihood of the first beam 106 and the second beam 108 from moving out of a generally coplanar alignment.

The first beam 106 and the first spring 110 may be crimped to secure the first spring 110 first end portion 126 in the first beam 106 spring cavity 132. Crimping the first beam 106 and the first spring 110 may include plastically deforming a portion of the first beam 106 and/or a portion of the first spring 110. The first beam 106 may include an outer wall 140 at least partially defining the spring cavity 132. The outer wall 140 may be disposed generally opposite a clamping surface 122 of the first beam 106. The outer wall 140 may include an outwardly facing recess 142. Crimping the first beam 106 and the first spring 110 may include receiving a tool 138 at least partially within the outwardly facing recess 142 of the outer wall 140. The first beam 106 may include an inner wall 144 at least partially defining the spring cavity 132. The inner wall 144 may be disposed generally towards a clamping surface 122 of the first beam 106. The inner wall 144 may include a cavity recess 146 within the spring cavity 132. Crimping the first beam 106 and the first spring 110 may include deforming at least a portion of the first end portion 126 of the first spring 110 into the cavity recess 146. Similar operations for assembling and securing components may be performed for other connections between beams and springs (e.g., crimp connections), and repeated description is omitted for brevity.

Some example methods of occluding an anatomical structure 10 according to at least some aspects of the present disclosure may include one or more of the following operations. An exclusion device may be delivered to a surgical site in a closed configuration. The exclusion device may include a first beam, a second beam, at least one spring operatively coupled to the first beam and the second beam to exert a closing force on the first beam and the second beam, the at least one spring operatively coupled to the first beam by a crimp connection. The exclusion device may be reconfigured from the closed configuration to an open configuration. The exclusion device may be positioned around an anatomical structure. The exclusion device may be reconfigured into the closed configuration to at least partially occlude the anatomical structure.

Reconfiguring the exclusion device into the closed configuration may include allowing the closing force exerted by the at least one spring to move the first beam and the second beam into the closed configuration. The method may further include detaching the exclusion device from an application instrument, withdrawing the application instrument, and/or maintaining the exclusion device in the closed configuration using the at least one spring.

The exclusion device may include a left atrial appendage occlusion clip. Positioning the exclusion device around the anatomical structure may include positioning the left atrial appendage occlusion clip around a left atrial appendage. At least partially occluding the anatomical structure may include at least partially occluding the left atrial appendage.

Figure 14:
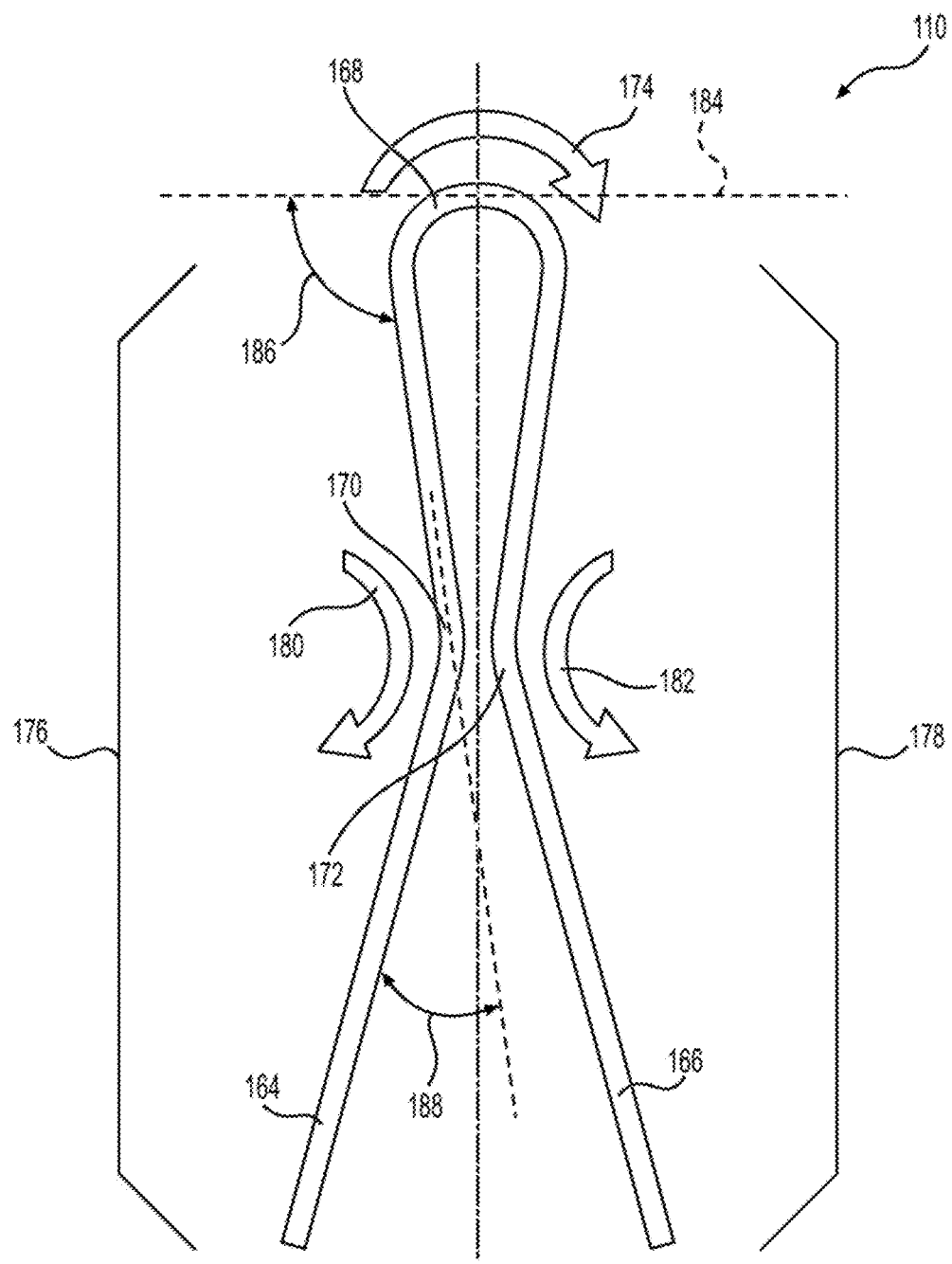
FIG. 14 is detailed elevation view of an example first spring.

FIG. 14 is detailed elevation view of an example first spring 110 according to at least some aspects of the present disclosure. Although the following description focuses on the first spring 110 of the exclusion device 100 (FIG. 1), the second spring 112 may be substantially similar to the first spring 110. Accordingly, the following description may also generally apply to the second spring 112. For the avoidance of doubt, FIG. 13 illustrates the example first spring 110 in a relaxed condition (e.g., without any externally applied forces). Dimensions, which are merely examples, are indicated in inches.

In the illustrated embodiment, the first spring 110 is generally U-shaped and includes a first end portion 164 and a second end portion 166 generally opposite a connecting portion 168. Interposing the connecting portion 168 and the first end portion 164 is a first reverse bend portion 170. Interposing the connecting portion 168 and the second end portion 166 is a second reverse bend portion 172. Between the connecting portion and the reverse bend portions 170, 172, the first spring 110 may be generally converging. Between the reverse bend portions 170, 172 and the end portions 164, 166, the first spring 110 may be generally diverging. In the illustrated embodiment, when the exclusion device 100 is assembled, the reverse bend portions 170, 172 may be configured to provide a spring pre-load (e.g., a closed-bias pre-load).

In some example embodiments, the first spring 110 may be substantially coplanar. That is, other than the thickness of the spring material forming the first spring 110, the spring may be substantially two-dimensional. Accordingly, the first spring 110 may exert forces substantially in only two dimensions, and there is generally no shearing action when the first spring 110 returns to its relaxed condition. In alternative embodiments, the first spring 110 may be non-coplanar. For example, a portion of the first spring 110 may cross over another portion of the first spring 110. In some such embodiments, the exclusion device 100 may be configured to provide additional stability due to the spring force in the third dimension.

In operation, some example first springs 110 may act as a combination of spring types. For example, the generally rounded connecting portion 168 of the first spring 110 may act generally as a torsion spring. The torsional moment associated with this portion of the first spring 110 is indicated by arrow 174. The elongated leg portions 176, 178 (e.g., the portions extending from the connecting portion 168 and including the first end portion 164 and the second end portion 166) may act as cantilever springs. The bending moments associated with these portions of the first spring 110 are indicated by arrows 180, 182.

The first spring 110 may include a first bend in the connecting portion 168. Each side of the first bend may be at an angle 186 relative to a reference line 184. For example, angle 186 may be about 98 degrees. The first spring 110 may include a second bend in the first reverse bend portion 170. The second bend may be at an angle 188 relative to the portion proximate the first bend. For example, angle 188 may be about 23 degrees. The second reverse bend portion 172 may be generally similar, but opposite in direction. Between the bends, the first spring 110 may be generally straight.

Figure 15:
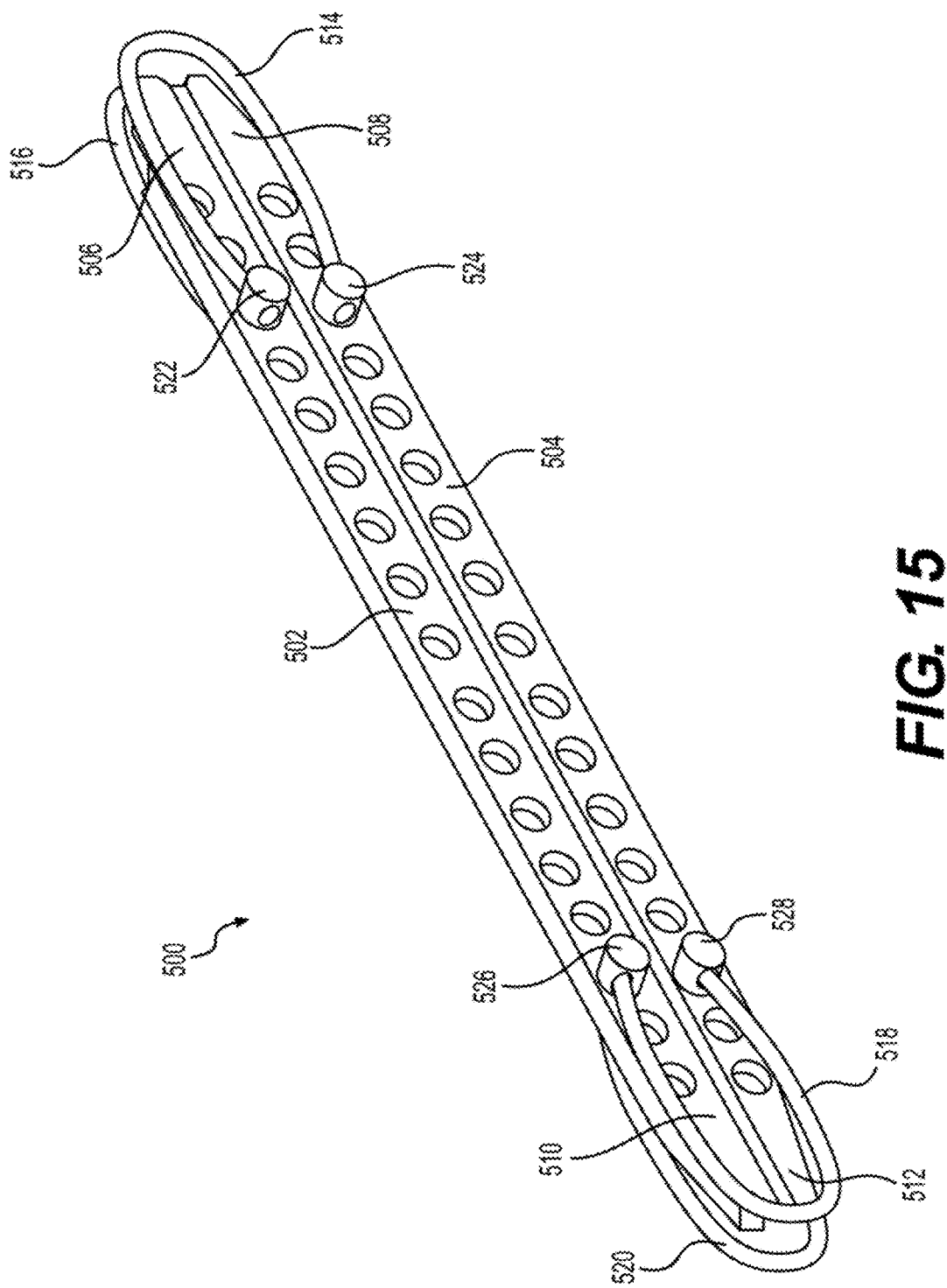
FIG. 15 is a perspective view of an alternative example exclusion device, in the closed configuration and without a cover.

FIG. 15 is a perspective view of an alternative example exclusion device 500, in the closed configuration and without a cover, in accordance with at least some aspects of the present disclosure. Exclusion device 500 is generally similar to the exclusion device 100 described above, and repeated description of components in common is omitted for brevity.

In the illustrated embodiment, the exclusion device includes a first beam 502 and a second beam 504. Each beam 502, 504 has a respective first end 506, 508 and second end 510, 512. The first beam 502 and the second beam 504 are coupled together by generally U-shaped springs 514, 516, 518, 520. The first spring 514 and the second spring 516 are coupled to the beams 502, 504 inward from their respective first ends 506, 508. The third spring 518 and the fourth spring 520 are coupled to the beams 502, 504 inward from their respective second ends 510, 512. Accordingly, each end 506, 508, 510, 512 of each beam 502, 504 is coupled to the other beam 502, 504 by two springs 514, 516, 518, 520, for a total of four springs 514, 516, 518, 520 coupling the beams 502, 504 together.

In the illustrated embodiment, the springs 514, 516, 518, 520 are coupled to the beams 502, 504 by pivots 522, 524, 526, 528, which extend laterally through the beams 502, 504 and/or are rotatable relative to the beams 502, 504. Specifically, the first spring 514 and the second spring 516 are coupled to the first beam 502 by the first pivot 522 and to the second beam 504 by the second pivot 524. The third spring 518 and the fourth spring 520 are coupled to the first beam 502 by the third pivot 526 and to the second beam 504 by the fourth pivot 528. In some alternative example embodiments, the springs 514, 516, 518, 520 may be coupled to the beams 502, 504 by posts which are generally similar to the pivots 522, 524, 526, 528, but which are secured against rotation relative to the beams 502, 504. In some such embodiments, the beams 502, 504 may be less likely to move out of alignment (e.g., parallelograming).

Generally, the four-spring exclusion device 500 of FIG. 15 may allow the use of smaller springs, subject to lower stresses, than the two-spring exclusion device 100 of FIG. 2 to achieve similar acceptable clamping forces. Additionally, in some example embodiments, some four-spring exclusion devices 500 may utilize simpler beam geometry as compared to the two-spring exclusion device 100. Accordingly, some beams 502, 504 of four-spring exclusion devices 500 may be manufactured using stamping, laser cutting, water jet cutting, and/or machining processes.

In some example embodiments, springs may be constructed from Nitinol. The present disclosure contemplates that some Nitinol alloys may have superelastic properties, which may be advantageous for some spring applications. The present disclosure contemplates that some springs constructed from some Nitinol alloys may exert a higher force when opening than when closing. That is, the unloading force may be less than the loading force.

The present disclosure contemplates that some springs constructed from some Nitinol alloys may exert greater forces at typical body temperatures (e.g., about 37 C) than at typical room temperatures (e.g., about 20 C). For example, in the illustrated embodiments, the springs exert about 60% more force at typical body temperatures than at typical room temperatures. As a result, some example exclusion devices may exert larger forces on the anatomical structure 10 after implantation (e.g., at about body temperature) than the force applied by the application instrument 300 to open the exclusion device prior to implantation (e.g., at about room temperature).

The present disclosure contemplates that the strength of Nitinol may degrade when it is cycled, particularly when it is cycled close to the yield strength. Accordingly, the springs 110, 112, 514, 516, 518, 520 may be designed so that an expected number reconfigurations between the closed configuration and the open configuration (e.g., 100 cycles) will not reduce the strength of the springs 110, 112, 514, 516, 518, 520 below a desired specification. Further, the present disclosure contemplates that Nitinol strength degradation due to cycling may be reduced with resting time. For example, some Nitinol components may recover approximately 90% of full strength after several days. Accordingly, much of any strength degradation caused by cycling during manufacturing of the exclusion device 100, 500 may be recovered by the time the exclusion device 100, 500 is received by a user.

In other example embodiments, springs may be constructed from stainless steel, polymers, or any other suitable biocompatible elastic materials.

Some example methods of making exclusion devices 100 for anatomical structure may include one or more of the following operations. A first spring 110 may be operatively connected between a first beam 106 and a second beam 108 to exert a closing force on the first beam 106 and the second beam 108. The first spring 110 may be generally U-shaped and comprises a respective first end portion 164 and a respective second end portion 166 generally opposite a connecting portion 168.

In some example embodiments, the method may further include operatively connecting a second spring 112 between the first beam 106 and the second beam 108 to exert the closing force on the first beam 106 and the second beam 108. The second spring 112 may be generally U-shaped and may comprise a respective first end portion 164 and a respective second end portion 166 generally opposite a respective connecting portion 168.

Some example methods of occluding an anatomical structure may include one or more of the following operations. An exclusion device 100 may be delivered to a surgical site in a closed configuration. The exclusion device 100 may include a first beam 106, a second beam 108, and a first spring 110 operatively coupled to the first beam 106 and the second beam 108 to exert a closing force on the first beam 106 and the second beam 108. The first spring 110 may be generally U-shaped and/or may include a first end portion 164 and a second end portion 166 generally opposite a connecting portion 168. The first spring 110 may include a first reverse bend portion 170 between the connecting portion 168 and the first end portion 164 and a second reverse bend portion 172 between the connecting portion 168 and the second end portion 166. The method may include reconfiguring the exclusion device 100 from the closed configuration to an open configuration. The method may include positioning the exclusion device 100 around an anatomical structure 10. The method may include reconfiguring the exclusion device 100 into the closed configuration to at least partially occlude the anatomical structure 10.

In some example embodiments, the method may further include detaching the exclusion device 100 from an application instrument 300. The method may include withdrawing the application instrument 300. The method may include maintaining the exclusion device 100 in the closed configuration using the first spring 110.

In some example embodiments, the closing force exerted by the first spring 110 may vary with a temperature of the first spring 110. The method may include increasing the closing force exerted by the first spring 110 by increasing the temperature of the first spring 110.

In some example embodiments, the exclusion device 100 may include a left atrial appendage occlusion clip. Positioning the exclusion device 100 around the anatomical structure 10 may include positioning the left atrial appendage occlusion clip around a left atrial appendage. At least partially occluding the anatomical structure 10 may include at least partially occluding the left atrial appendage.

Figure 16:
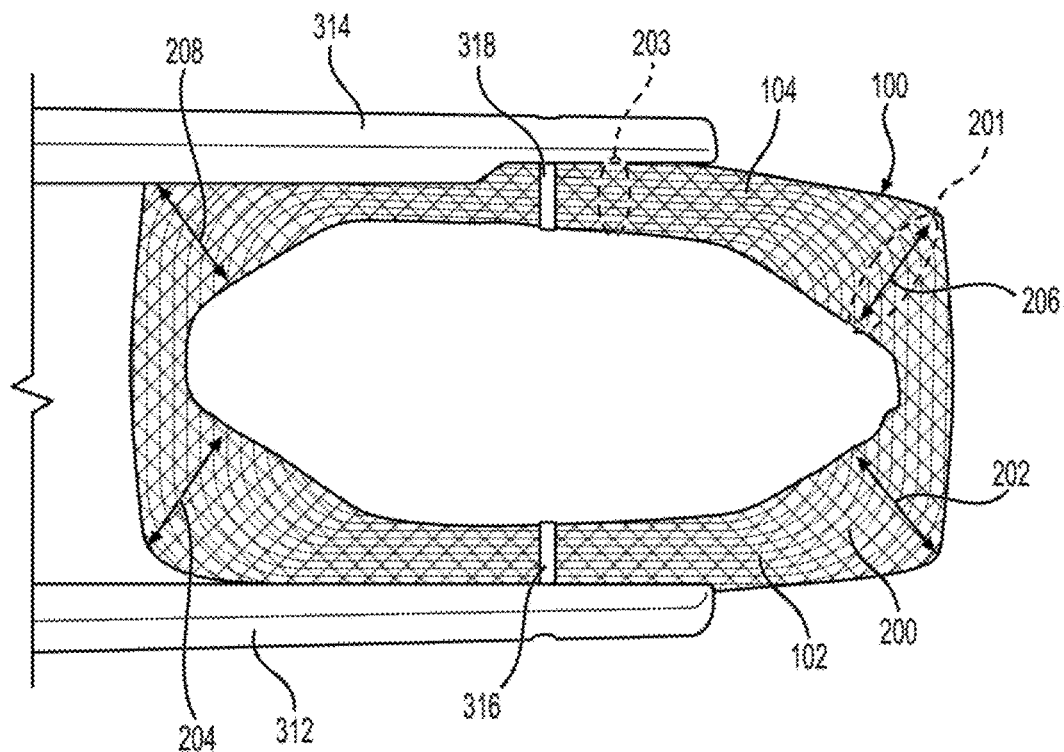
FIG. 16 is a detailed elevation view of the jaws of the exclusion device application instrument of FIG. 4 with the exclusion device of FIG. 1 in an open configuration.
Figure 17:
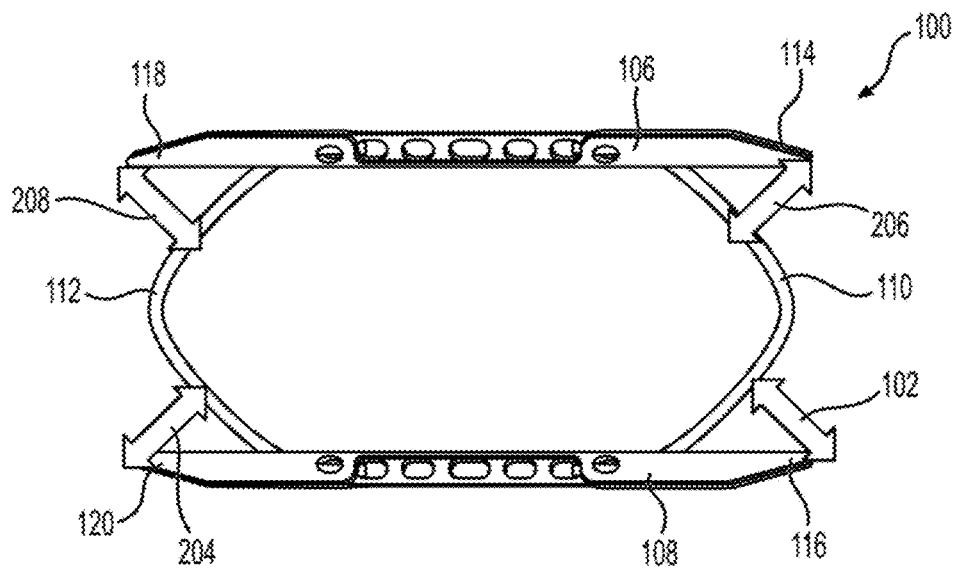
FIG. 17 is an elevation view of the exclusion device of FIG. 1 in the open configuration and without the cover.

FIG. 16 is a detailed elevation view of the jaws 312, 314 of the exclusion device application instrument 300 of FIG. 4 with the exclusion device 100 of FIG. 1 in an open configuration, and FIG. 17 is an elevation view of the exclusion device 100 of FIG. 1 in the open configuration and without the cover 200, all in accordance with at least some aspects of the present disclosure. Referring to FIGS. 1 and 4 (closed configuration) and FIGS. 5, 16, and 17 (open configuration), in the illustrated embodiment, portions of the cover 200 are stretched when the exclusion device 100 is reconfigured from the closed configuration to the open configuration. In particular, in this example embodiment, portions of the generally tubular cover 200 generally between the ends 114, 116, 118, 120 of the beams 106, 108 and the springs 110, 112, as indicated by arrows 202, 204, 206, 208 are circumferentially stretched to a stretched circumference 201 that is a multiple of the relaxed circumference 203. As used herein, "circumference" may refer to a length of a perimeter of a cross section, taken generally perpendicularly to a local longitudinal direction, of a generally tubular body. The cross section may be non-circular, such as when the cover 200 is stretched between the beams 106, 108 and the springs 110, 112 as shown in FIGS. 5 and 6. In the illustrated embodiment, portions of the cover 200 are stretched to a stretched circumference 201 of about two times (2×) to about three times (3×) of the relaxed circumference 203 when the exclusion device 100 is in the open configuration. In the illustrated embodiment, in the open configuration, the circumference of the entire generally toroidal cover 200 may stretch to less than about 2× of its relaxed circumference, even when particular generally tubular portions of the cover 200 are stretched to a stretched circumference 201 of about 2× to about 3× of their relaxed circumference 203.

Figure 18:
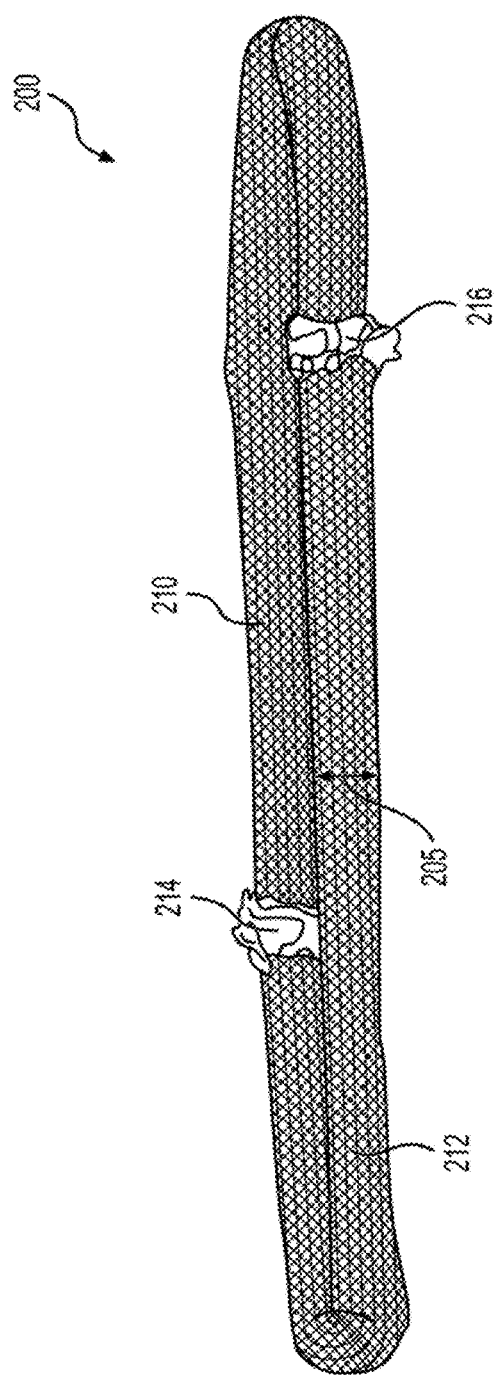
FIG. 18 is a perspective view of an example cover.

FIG. 18 is a perspective view of an example cover 200, according to at least some aspects of the present disclosure. In the illustrated embodiment, the cover 200 is constructed from a woven fabric, such as a circular knit fabric. For example, a fabric having a circular warp knit braid with about 35 courses per inch (CPI) to about 45 CPI, such as about 38 CPI may be utilized. The fabric may be woven from a biocompatible material, such as texturized polyethylene terephthalate (PET) yarn.

In some example embodiments, the fabric of the cover 200 may define a generally tubular shape which is configured to extend generally toroidally around the beams 106, 108 and springs 110, 112. The fabric of the cover 200 may be heat set on a mandrel to maintain its generally tubular form. In some example embodiments, the fabric may be generally flexible and compliant, so the cross section of the generally tubular shape may vary with the configuration of the exclusion device 100 and/or with the shape of the components within the cover 200.

In alternative example embodiments, the cover 200 may be constructed from other woven fabrics having different weave patterns and/or from non-woven fabrics. In alternative example embodiments, the cover 200 may comprise multiple layers (plies) of texturized yarn, for example. The present disclosure contemplates that a large number of layers may add bulk to the weave and/or may reduce flexibility. Accordingly, some example embodiments providing relatively small profile exclusion devices 100 may include covers 200 including relatively few layers of fabric.

Referring to FIG. 18, in some example embodiments, the cover 200 may be constructed from two or more sections 210, 212, which may be joined together to secure the cover 200 over the underlying structure of the exclusion device 100 in a generally toroidal manner. For example, the first section 210 may be welded to the second section 212 at a first joint 214 and/or at a second joint 216. Similarly, a cover 200 formed from a single section of tubular fabric may be welded to itself at a similar joint to form a generally toroidal shape. In some example embodiments, one of the first section 210 and the second section 212 (or ends of a single section) may be overlapped with respect to the other, and one or more welds may extend generally radially to join the first section 210 and the second section 212. Example welding methods include, without limitation, ultrasonic welding and heat welding. More generally, various example attachment methods (e.g., welding) may be selected and configured to minimize thickness and/or to minimize disruption of the tissue ingrowth function of the cover 200.

Figure 19:
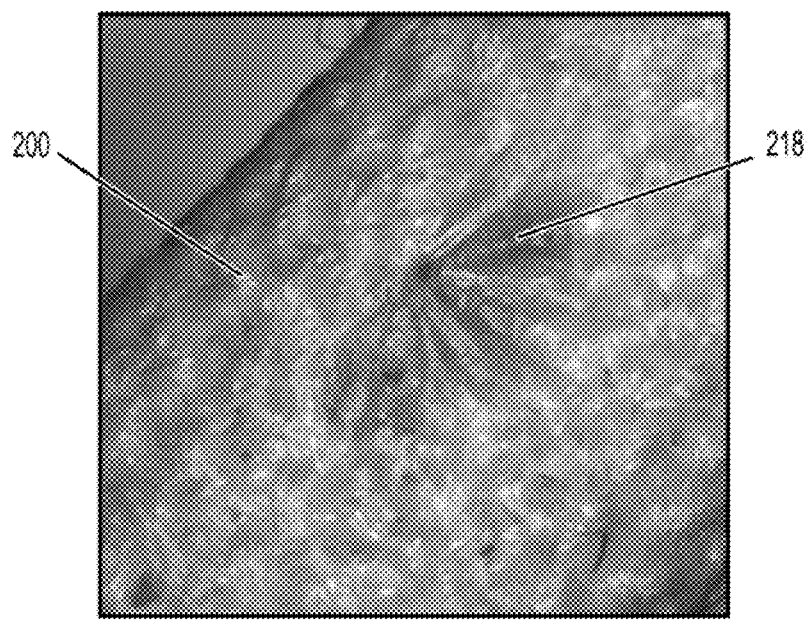
FIG. 19 is a detailed view of an example ultrasonic weld in an exclusion device cover.
Figure 20:
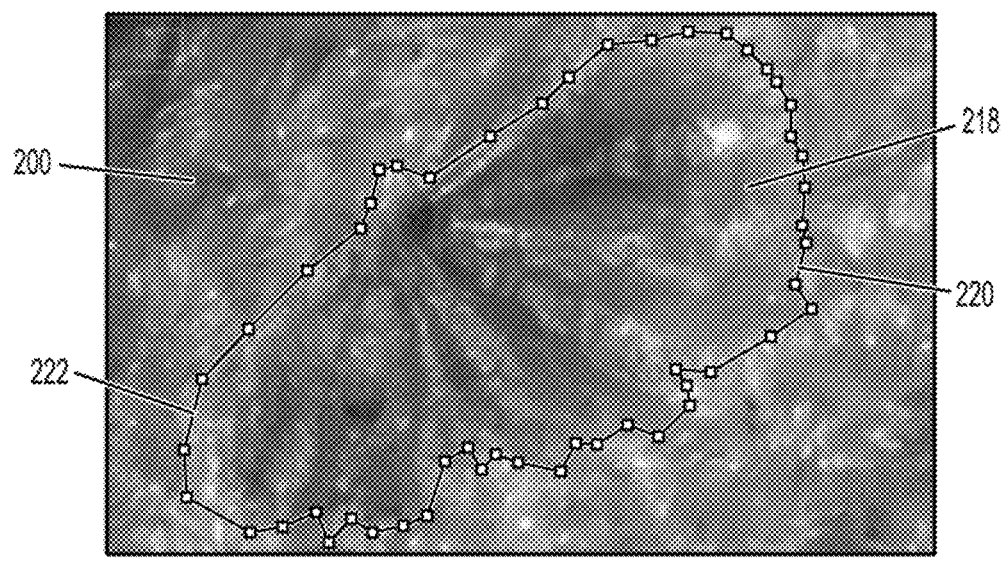
FIG. 20 is a detailed view of an example ultrasonic weld in an exclusion device cover.

FIGS. 19 and 20 are detailed views of an example ultrasonic weld 218 in an exclusion device 100 cover 200, all in accordance with at least some aspects of the present disclosure. Referring to FIGS. 18-20, the ultrasonic weld 218 may be used at one of the joints 214, 216 to couple the first section 210 and the second section 212. Generally, the ultrasonic weld 218 is relatively small in size and/or has an irregular periphery 220, which may facilitate tissue ingrowth into the cover 200 near the weld 218. The ultrasonic weld 218 may be relatively small compared to the relaxed diameter 205 of the cover 200. For example, in one embodiment, the relaxed diameter 205 of the cover 200 may be about 3.0 mm and the size 222 of the ultrasonic weld 218 may be about 2.0 mm². Accordingly, tissue ingrowth into the cover 200 and/or beams 106, 108 may be minimally affected proximate the joints 214, 216. The ultrasonic weld 218 may be created at a position adjacent to a generally flat portion of one of the beams 106, 108, such as by using the beam 106, 108 in cooperation with the ultrasonic horn to create the weld 218. In various example embodiments, the pressure, power, duration, and horn geometry may be adapted to produce the desired ultrasonic weld 218.

Some example methods of making an exclusion device 100 for an anatomical structure 10 may include one or more of the following operations. The clamping portion 102, 104 of an exclusion device 100 comprising a beam 106, 108 and a biocompatible fabric cover 200 may be assembled. The cover 200 may be secured on the beam 106, 108 by ultrasonic welding a first portion of the cover 200 to a second portion of the cover 200. The ultrasonic welding operation may include overlapping the first portion of the cover 200 and the second portion of the cover 200. The ultrasonic welding operation may include applying ultrasonic energy to the overlapped first portion of the cover 200 and the second portion of the cover 200 to create at least one ultrasonic weld 218 configured and arranged to facilitate tissue ingrowth into the cover 200 near the ultrasonic weld 218. The overlapping the first portion of the cover and the second portion of the cover operation may include positioning the second portion of the cover generally radially within the first portion of the cover. The ultrasonic welding operation may include applying ultrasonic energy at about 40 kHz.

In other example embodiments, alternative methods of coupling portions of the cover 200 may be employed. For example, some embodiments may utilize hand-sewn suturing to couple portions of the cover 200. In other example embodiments, heat welding may be utilized.

Figure 21:
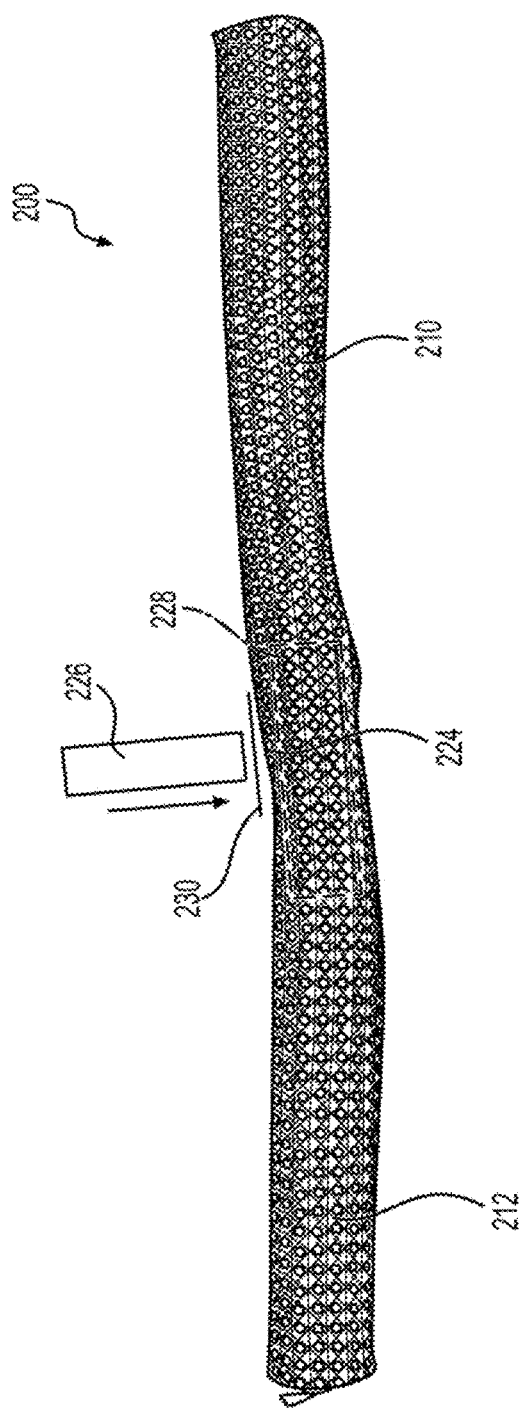
FIG. 21 is a detailed perspective view of a portion of a cover including an example heat weld.

FIG. 21 is a detailed perspective view of a portion of a cover 200 including an example heat weld 224, according to at least some aspects of the present disclosure. In this example embodiment, an externally applied heat source (e.g., a heating element 226) may be used in cooperation with an inner mandrel 228 (e.g., a generally flat portion of a beam 106, 108 (FIG. 3), such as outwardly facing surfaces 158, 160 (FIG. 13)) to form the heat weld 224. In some example embodiments, a protective sheet 230 may be positioned between the heating element 226 and the fabric of the cover 200. The protective sheet 230 may include polytetrafluoroethylene. Use of the protective sheet 230 in the heat welding operation may reduce overheating, stringing, discoloration, and/or burns. In this example embodiment, a portion of the second section 212 of the cover 200 is positioned generally radially within a portion of the first section 210 of the cover 200 in an overlapping fashion. The heat weld 224 is formed in the overlapped portion of the cover 200.

Some example methods of making an exclusion device 100 for an anatomical structure 10 may include one or more of the following operations. A clamping portion 102, 104 of an exclusion device 100 comprising a beam 106, 108 and a biocompatible fabric cover 200 may be assembled. The cover 200 may be secured on the beam 106, 108 by heat welding a first portion of the cover 200 to a second portion of the cover 200. The heat welding operation may include overlapping the first portion of the cover 200 and the second portion of the cover 200. The heat welding operation may include applying heat to the overlapped first portion of the cover 200 and the second portion of the cover 200 to create at least one heat weld 224 configured and arranged to facilitate tissue ingrowth into the cover 200 proximate the at least one heat weld 224. The heat welding operation may include positioning a protective sheet 230 between a heat source 226 and the cover 200 and/or applying heat to the first portion of the cover 200 and the second portion of the cover 200 through the protective sheet 230 using the heat source 226.

Figure 22:
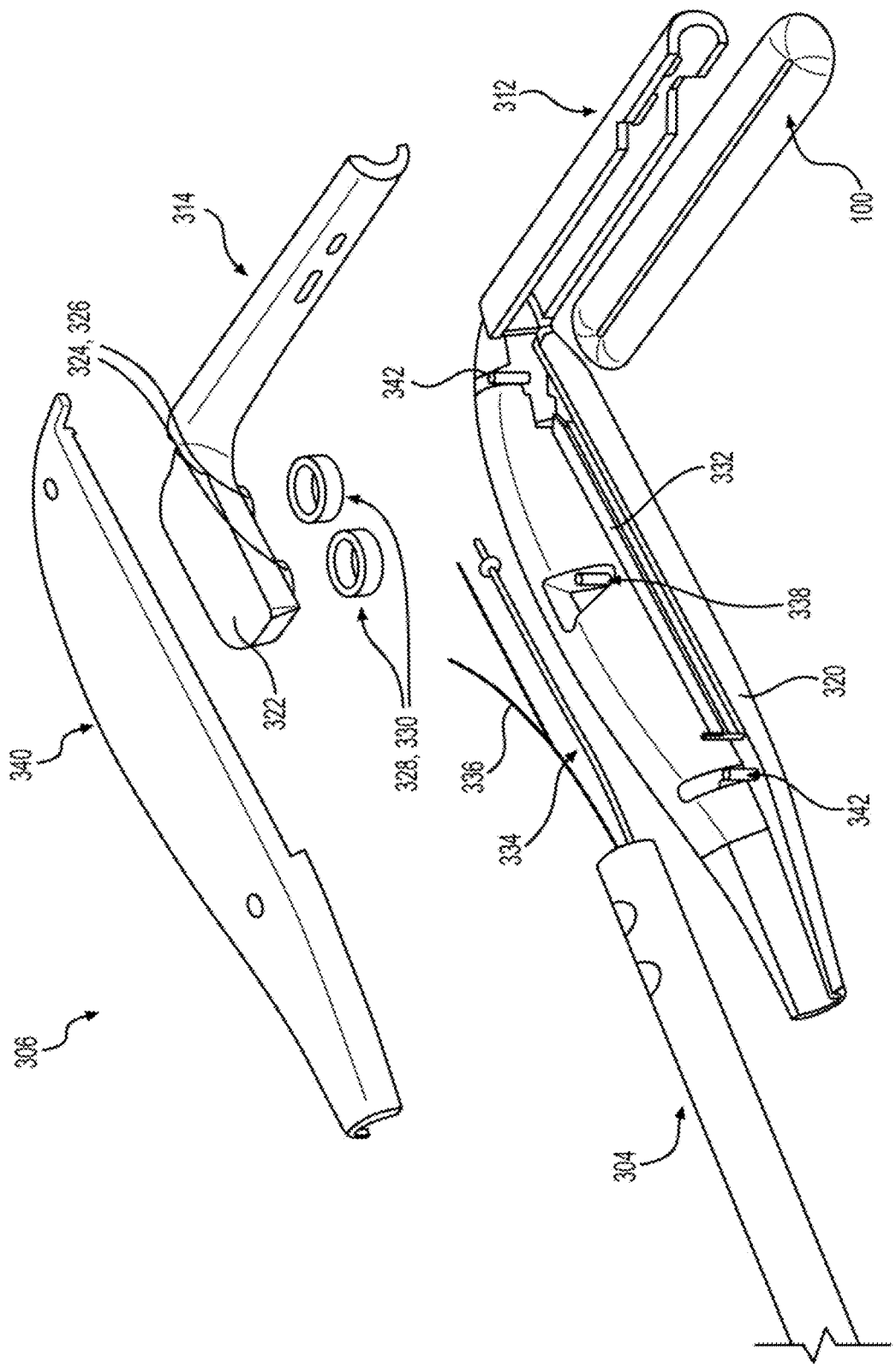
FIG. 22 is an exploded view of the end effector of FIGS. 4 and 5.

FIG. 22 is an exploded view of the end effector 306 of FIGS. 4 and 5, according to at least some aspects of the present disclosure. In the illustrated embodiment, the end effector 306 includes a head 320, which is configured to be disposed distally on the shaft 304. The stationary jaw 312 is fixedly disposed on the head 320, and the movable jaw 314 is movably disposed on the head 320. In this example embodiment, the stationary jaw 312 is integrally formed with the head 320. In alternative embodiments, the stationary jaw 312 may include a separately formed component that is affixed to the head 320.

In the illustrated embodiment, the movable jaw 314 is integrally formed with a traveler 322. In alternative example embodiments, the movable jaw 314 may include a separately formed component that is affixed to the traveler 322. The traveler 322 is movably disposed on the head 320 to produce a generally parallel opening motion of the exclusion clip 100. The end effector 306 may include at least one friction reduction element operatively interposing the traveler 322 and the head 320. For example, in this embodiment, the traveler 322 includes posts 324, 326, to which one or more friction reduction elements, such as ball bearings 328, 330, are coupled. The ball bearings 328, 330 engage a track 332 on the head 320 to provide generally low-friction, proximal-distal motion of the second jaw 314. Other embodiments may include one or more alternative friction reduction elements, such as one or more rollers and/or one or more low-friction sliders.

The present disclosure contemplates that, generally, it may be desirable to reduce friction and/or other forces opposing opening and/or closing of the exclusion device 100. For example, a relatively low force application requirement for the user may be more comfortable and/or more controllable for users. Additionally, in the illustrated embodiment, the springs 110, 112 of the exclusion device 100 provide the primary force that moves the exclusion device 100 from the open configuration to the closed configuration. Accordingly, smooth operation of the application instrument 300 in the closing direction may be improved when the resistance to closing (e.g., friction in the end effector 306) is reduced.

Referring to FIGS. 4, 5, 16, and 22, in the illustrated embodiment, an opening cable 334 extends through the shaft 304 and operatively couples the first actuator 308 and the end effector 306. Specifically, the opening cable 334 is operatively coupled to the traveler 322 to pull the traveler 322 generally proximally to open the exclusion device 100. The opening cable 334 may include, for example, a multi-stranded stainless steel cable. The opening cable 334 may be constructed with a pre-attached ball and/or loop to facilitate assembly of the application instrument 300, such as without a crimping fixture. The present disclosure contemplates that variations in the length of the opening cable 334 may affect the aperture of the jaws 312, 314 and/or the exclusion device 100. Accordingly, manufacturing tolerances may be established to ensure proper operation of the application instrument 300.

In the illustrated embodiment, a deployment cable 336 extends through the shaft 304 and operatively couples the second actuator 310 and the end effector 306. Specifically, the deployment cable 336 is operatively coupled to the sutures 316, 318 to deploy the exclusion device 100. The deployment cable 336 may include, for example, a multi-stranded stainless steel cable. The deployment cable 336 may include individual portions extending to respective jaws 312, 314. In some example embodiments, movement of the movable jaw 314 between the open and closed configurations may affect the tension, slack, and/or routing of the deployment cable 336. Accordingly, some example embodiments may include one or more cable management elements. For example, the illustrated embodiment includes a cable management pin 338 disposed on the head 320. The deployment cable 336 is routed around the cable management pin 338 so that excessive slack is not created in the deployment cable 336 when the movable jaw 314 is in the open configuration. More generally, the cable management elements, such as the cable management pin 338, may allow the movable jaw 314 to move without causing relative movement of the deployment cable 336.

Referring to FIG. 22, in the illustrated embodiment, the end effector 306 includes a cover 340 positioned generally over the traveler 322 and track 332 mechanism. In some example embodiments, the cover 340 may engage the head 320 to provide a generally smooth exterior surface for the end effector 306. The cover 340 may be secured to the head 320 by one or more threaded fasteners (e.g., screws), one or more welds, and/or one or more rivets 342. In the illustrated embodiment, the rivets 342 are secured using a swage riveting technique and/or an orbital riveting technique, which may provide a generally smooth exterior surface (e.g., lacking sharp edges that might act as a catch point to cut or snag tissue) and which may minimize the risk of loose parts. In the illustrated embodiment, the rivets 342 are built-in to the head 320; however, in some alternative embodiments, the rivets 342 may be provided as separate components.

Figure 23:
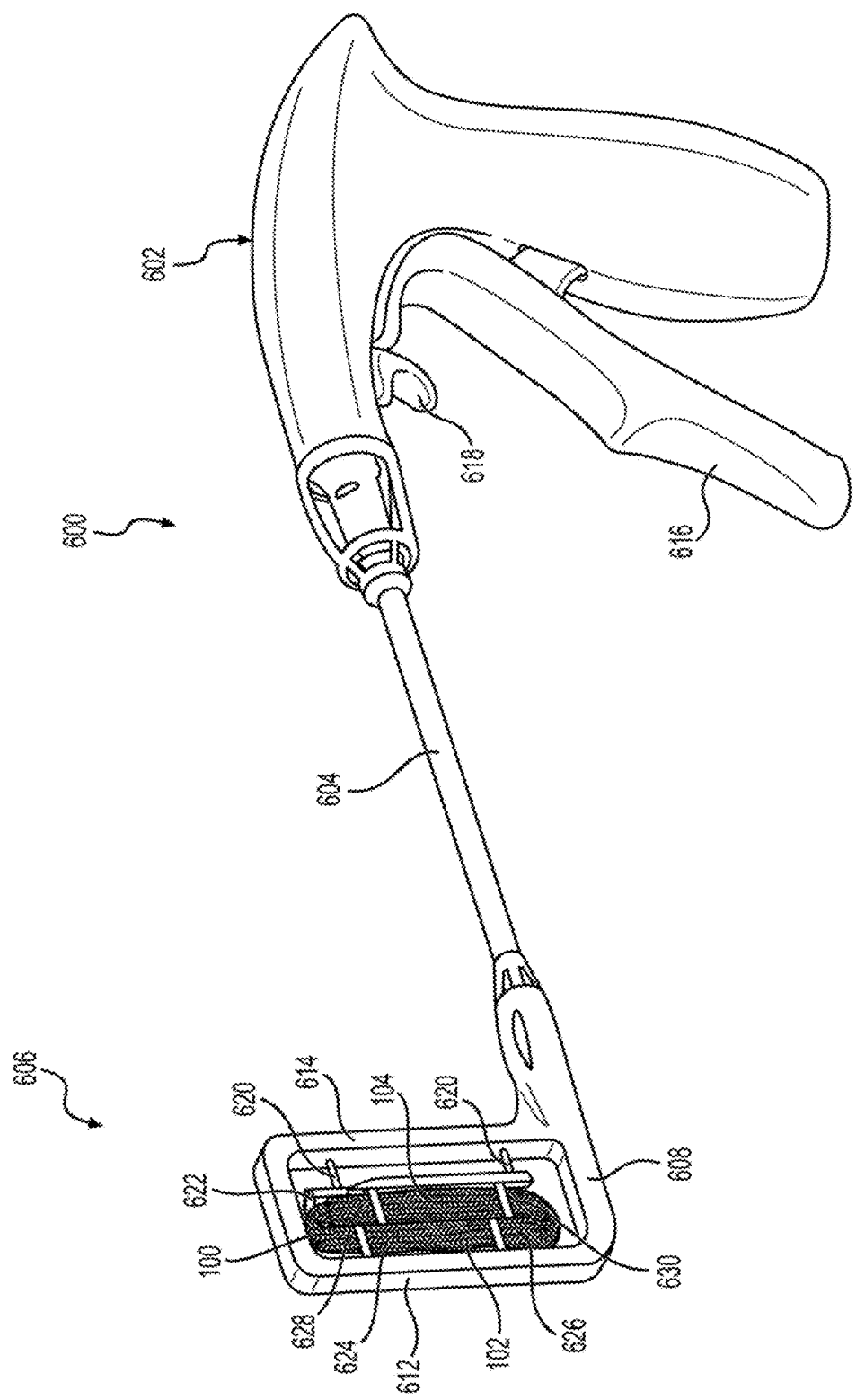
FIG. 23 is a perspective view of an alternative example exclusion device application instrument; all in accordance with at least some aspects of the present disclosure.

FIG. 23 is a perspective view of an alternative example exclusion device 100 application instrument 600, in accordance with at least some aspects of the present disclosure. This example application instrument 600 is generally similar to the application instrument 300 of FIGS. 4 and 5, and repeated description of similar components and functions is omitted for brevity. In the illustrated embodiment, the application instrument 600 includes a generally proximal handle portion 602, an elongated, malleable shaft 604 extending distally from the handle portion 602, and an end effector 606 disposed distally on the shaft 604.

In this example embodiment, the end effector 606 comprises a generally loop-shaped frame 608, which is configured to hold the exclusion device 100. In contrast to the movable jaw 314 arrangement of FIGS. 4 and 5, in this example embodiment, the frame 608 is generally rigid and non-movable. In the illustrated embodiment, one clamping portion 102 of the exclusion device 100 is releasably secured to a first segment 612 of the frame (e.g., a distal segment in this embodiment). The other clamping portion 104 is releasably secured to a second segment 614 of the frame 608 (e.g., a proximal segment in this embodiment), which may be generally opposite the first segment 612, forming a generally rectangular opening for the exclusion device 100.

In the illustrated embodiment, the end effector 606 is arranged to reconfigure the exclusion device 100 between open and closed configurations and to release the exclusion device 100 based on operation of one or more actuators 616, 618 on the handle portion 602 by the user. For example, operation of the first actuator 616 may pull one or more connecting elements 620 to reconfigure the exclusion device 100 to the open configuration. In some example embodiments, the end effector 606 may be configured for substantially parallel opening of the first clamping portion 102 and second clamping portion 104 of the exclusion device 100. In some example embodiments, one or more strongback elements 622 may operatively interpose the frame 608 and the exclusion device 100. In the illustrated embodiment, the exclusion device 100 is releasably retained in the frame 608 by sutures 624, 626, 628, 630. Operation of the second actuator 618 may release the sutures 624, 626, 628, 630, which may deploy the exclusion device 100.

In some example embodiments, various components of the end effector 306 may be constructed from one or more metals and/or metal alloys, such as 17-4 stainless steel. Some components may be formed using metal injection molding processes. The present disclosure contemplates that metal injection molding is generally a cost-effective choice for tight tolerance parts with a good surface finish that minimizes secondary finishing. Further, metal injection molding allows for various metal selections.

In alternative example embodiments, various components of the end effector 306 may be constructed from one or more plastics. For example, various components of the end effector 306 may be constructed from plastics with high strength, low deflection properties. Some example plastic materials may include filler materials, such as glass or carbon fiber, to improve the structural capabilities. Thermoplastics, such as glass filled polyamide and/or polyetherimide, may be utilized. In some circumstances, thermoplastic parts may be less expensive than similar metal parts; however, plastics may not be as strong as metals (e.g., 17-4 stainless steel) so plastic components may need to be larger than corresponding metal components to provide similar strengths.

Some example methods of making an application instrument 300 for an exclusion device 100 for an anatomical structure 10 may include one or more of the following operations. An end effector 306 may be assembled, where the end effector 306 includes a head 320 configured to be disposed distally on a shaft 304, a stationary jaw 312 fixedly disposed on the head 320 and configured to releasably couple to a first clamping portion 102 of an exclusion device 100 for an anatomical structure 10, the exclusion device 100 being biased in a closing direction, and a movable jaw 314 movably disposed on the head 320 and configured to releasably couple to a second clamping portion 104 of the exclusion device 100 for the anatomical structure 10. The end effector 306 may be coupled distally on the shaft 304. A handle portion 302 may be coupled proximally on the shaft 304.

In some example embodiments, a first actuator 308 on the handle portion 302 may be operatively connected to the end effector 306 so that the first actuator 308 is operative to move the movable jaw 314 to reconfigure the exclusion device 100 from the closed configuration to the open configuration. In some example embodiments, a second actuator 310 on the handle portion 302 may be operatively connected to the end effector 306 so that the second actuator 310 is operative to deploy the exclusion device 100 from the first jaw 312 and the second jaw 314. Operatively connecting the second actuator 314 on the handle portion 302 to the end effector 306 may include routing a deployment cable 336 around at least one cable management pin 338 configured to allow movement of the movable jaw 314 without relative movement of the deployment cable 338. Assembling the end effector 306 may include attaching a cover 340 to the head 320. Attaching the cover 340 to the head 320 may include riveting the cover 340 to the head 320.

Some example methods of using an application instrument 300 for an exclusion device 100 for an anatomical structure 10 may include one or more of the following operations. A first actuator 308 on a handle portion 302 of an application instrument 300 carrying an exclusion device 100 may be operated to reconfigure the exclusion device 100 into an open configuration. An end effector 306 of the application instrument 300 may be positioned to locate the exclusion device 100 on an anatomical structure 10. The first actuator 308 may be operated to reconfigure the exclusion device 100 into a closed configuration on the anatomical structure 10. A second actuator 310 on a handle portion 302 of the application instrument 300 may be operated to deploy the exclusion device 100 from the end effector 306.

In some example embodiments, the end effector 306 may include a head 320 configured to be disposed distally on a shaft 304, a stationary jaw 312 fixedly disposed on the head 320 and configured to releasably couple to a first clamping portion 102 of the exclusion device 100. The exclusion device 100 may be biased in a closing direction. A movable jaw 314 may be movably disposed on the head 320 and configured to releasably couple to a second clamping portion 104 of the exclusion device 100. Operating the first actuator 308 on the handle portion 302 of the application instrument 300 carrying the exclusion device 100 to reconfigure the exclusion device 100 into the open configuration may include moving the movable jaw 314 relative to the stationary jaw to reconfigure the exclusion device 100 from the closed configuration to the open configuration while the movable jaw 314 and the stationary jaw 312 are oriented generally in parallel. Operating the second actuator 310 on the handle portion 302 of the application instrument 300 to deploy the exclusion device 100 from the end effector 306 may include moving a deployment cable 336 around at least one cable management pin 338 configured to allow movement of the movable jaw 314 without relative movement of the deployment cable 336.

Unless specifically indicated, it will be understood that the description of the structure, function, and/or methodology with respect to any illustrative embodiment herein may apply to any other illustrative embodiments. More generally, it is within the scope of the present disclosure to utilize any one or more features of any one or more example embodiments described herein in connection with any other one or more features of any other one or more other example embodiments described herein. Accordingly, any combination of any of the features or embodiments described herein is within the scope of this disclosure.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope of the disclosure. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

What is claimed is:

1. An exclusion device, comprising:
   a first clamping portion;

a second clamping portion opposing the first clamping portion; and a biocompatible fabric cover at least partially sheathing at least one of the first clamping portion and the second clamping portion, the cover being generally tubular and defining a relaxed circumference when the first clamping portion and the second clamping portion are in a closed configuration;

wherein at least a portion of the cover is configured to stretch to a stretched circumference of about 2× to about 3× the relaxed circumference when the first clamping portion and the second clamping portion are reconfigured from the closed configuration to an open configuration.

2. The exclusion device of claim 1, wherein the exclusion device comprises a closed-biased left atrial appendage occlusion clip.

3. The exclusion device of claim 1, wherein cover is configured to promote tissue ingrowth.

4. The exclusion device of claim 1, wherein the cover comprises a circular knit warp weave fabric.

5. The exclusion device of claim 1, wherein the cover comprises woven polyethylene terephthalate yarn.

6. The exclusion device of claim 1, wherein the cover comprises at least one weld securing the cover on the at least one of the first clamping portion and the second clamping portion.

7. The exclusion device of claim 6, wherein the at least one weld comprises at least one ultrasonic weld.

8. The exclusion device of claim 6, wherein the at least one weld comprises at least one heat weld.

9. The exclusion device of claim 6, wherein the at least one weld is configured and arranged to facilitate tissue ingrowth into the cover near the at least one weld.

10. An exclusion device, comprising:
a first beam;
a second beam operatively coupled to the first beam by a first spring, the first spring being deformable between a first position and a second position, where the first position spaces the first beam and the second beam by a first distance, and where the second position spaces the first beam and the second beam by a second distance, where the first distance is greater than the second distance; and
a biocompatible cover longitudinally circumscribing the spring and at least a portion of the first and second beams;

wherein a first portion of the biocompatible cover is configured to at least double its widthwise dimension, perpendicular to a longitudinal dimension, responsive to the first spring moving between the first position and the second position, and where a second portion of the biocompatible cover generally maintains its widthwise dimension responsive to the first spring moving between the first position and the second position.

11. The exclusion device of claim 10, wherein the exclusion device further comprises a second spring operatively coupling the first beam and the second beam, where the exclusion device is biased by the first and second springs to force the first beam toward the second beam.

12. The exclusion device of claim 11, wherein the biocompatible cover longitudinally circumscribes the first beam, the second beam, the first spring, and the second spring in a toroidal shape.

13. The exclusion device of claim 10, wherein biocompatible cover is configured to promote tissue ingrowth.

14. The exclusion device of claim 10, wherein the biocompatible cover comprises a circular knit warp weave fabric.

15. The exclusion device of claim 10, wherein the biocompatible cover comprises woven polyethylene terephthalate yarn.

16. The exclusion device of claim 10, wherein the biocompatible cover includes a weld securing the biocompatible cover to at least one of the first beam and the second beam.

17. The exclusion device of claim 16, wherein the weld comprises an ultrasonic weld.

18. The exclusion device of claim 16, wherein the weld comprises a heat weld.

19. The exclusion device of claim 16, wherein the weld is configured and arranged to facilitate tissue ingrowth into the biocompatible cover near the weld.

20. The exclusion device of claim 10, wherein:
the first beam predominantly overlaps the second beam;
the first position of the first spring extends longitudinally beyond the first beam and the second beam;
the first and second beams extend longitudinally beyond the first spring so that the first spring is inset with respect to a terminal end of each of the first and second beams when the first spring is in the second position.

* * * * *